(12) United States Patent
Havenga et al.

(10) Patent No.: US 7,235,233 B2
(45) Date of Patent: *Jun. 26, 2007

(54) SEROTYPE 5 ADENOVIRAL VECTORS WITH CHIMERIC FIBERS FOR GENE DELIVERY IN SKELETAL MUSCLE CELLS OR MYOBLASTS

(75) Inventors: Menzo Jans Emco Havenga, Rijn (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 111 days.

This patent is subject to a terminal disclaimer.

(21) Appl. No.: 10/381,857

(22) PCT Filed: Sep. 25, 2001

(86) PCT No.: PCT/NL01/00703

§ 371 (c)(1),
(2), (4) Date: Aug. 13, 2003

(87) PCT Pub. No.: WO02/27006

PCT Pub. Date: Apr. 4, 2002

(65) Prior Publication Data

US 2004/0071660 A1    Apr. 15, 2004

Related U.S. Application Data

(60) Provisional application No. 60/235,665, filed on Sep. 26, 2000.

(30) Foreign Application Priority Data

Sep. 26, 2000    (EP) .................... 00203336

(51) Int. Cl.
| A01N 63/00 | (2006.01) |
| A01N 65/00 | (2006.01) |
| A01N 43/04 | (2006.01) |
| A61K 31/70 | (2006.01) |
| C12N 5/00 | (2006.01) |
| C12N 5/02 | (2006.01) |

(52) U.S. Cl. .............. 424/93.1; 424/93.21; 435/325; 514/44

(58) Field of Classification Search .............. None
See application file for complete search history.

(56) References Cited

U.S. PATENT DOCUMENTS

| 4,487,829 A | 12/1984 | Sharp et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,792,525 A | 12/1988 | Ruoslahti et al. |
| 4,797,368 A | 1/1989 | Carter et al. |
| 4,956,281 A | 9/1990 | Wallner et al. |
| 5,024,939 A | 6/1991 | Gorman |
| 5,096,815 A | 3/1992 | Ladner et al. |
| 5,166,320 A | 11/1992 | Wu et al. |
| 5,198,346 A | 3/1993 | Ladner et al. |
| 5,204,445 A | 4/1993 | Plow et al. |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,403,484 A | 4/1995 | Ladner et al. |
| 5,436,146 A | 7/1995 | Shenk et al. |
| 5,443,953 A | 8/1995 | Hansen et al. |
| 5,474,935 A | 12/1995 | Chatterjee et al. |
| 5,521,291 A | 5/1996 | Curiel et al. |
| 5,534,423 A | 7/1996 | Plasson et al. |
| 5,543,328 A | 8/1996 | Mcclelland et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,712,136 A | 1/1998 | Wickham et al. |
| 5,731,190 A | 3/1998 | Wickham et al. |

(Continued)

FOREIGN PATENT DOCUMENTS

| EP | 259212 | 8/1987 |
| EP | 1016726 | 12/1998 |
| EP | 99201545.3 | 5/1999 |
| EP | 1020529 | 11/1999 |
| EP | 0 978 566 A2 | 2/2000 |

(Continued)

OTHER PUBLICATIONS

Deonarain (1998) Expert Opin. Ther. Pat., 8: 53-69.*

(Continued)

*Primary Examiner*—Joseph Woitach
*Assistant Examiner*—Robert M. Kelly
(74) *Attorney, Agent, or Firm*—TraskBritt

(57) ABSTRACT

The invention provides means and methods for transduction of a skeletal muscle cell and/or a muscle cell specific precursor thereof. Provided is the use of a gene delivery vehicle derived from an adenovirus, having a tropism for said cells, for the preparation of a medicament. In a preferred aspect of the invention, said gene delivery vehicle comprises at least a tropism determining part of an adenoviral fiber protein of subgroup B and/or F. More preferably, said gene delivery vehicle comprises at least part of a fiber protein of an adenovirus of stereotype (11, 16, 35, 40 and/or 51) or a functional part, derivative and/or analogue thereof.

3 Claims, 6 Drawing Sheets

U.S. PATENT DOCUMENTS

Figure 1:
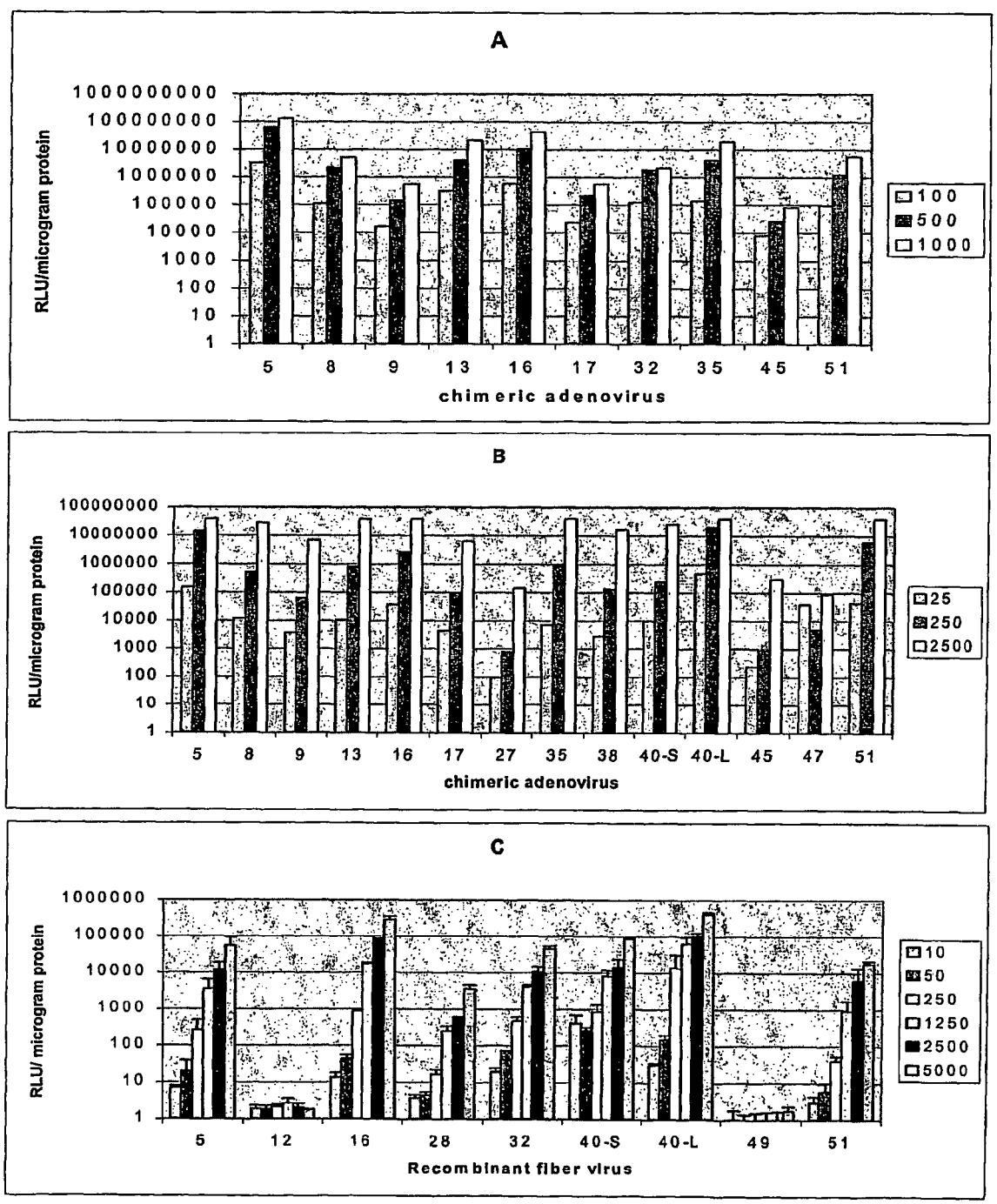

| | | | |
|---|---|---|---|
| 5,756,086 | A | 5/1998 | Mcclelland et al. |
| 5,770,442 | A | 6/1998 | Wickham et al. |
| 5,837,511 | A | 11/1998 | Flack-Pedersen et al. |
| 5,846,782 | A | 12/1998 | Wickham et al. |
| 5,849,561 | A | 12/1998 | Flack-Pedersen |
| 5,856,152 | A | 1/1999 | Wilson et al. |
| 5,871,727 | A | 2/1999 | Curiel |
| 5,871,982 | A | 2/1999 | Wilson et al. |
| 5,877,011 | A | 3/1999 | Armentano et al. |
| 5,922,315 | A | 7/1999 | Roy |
| 6,033,908 | A | 3/2000 | Bout et al. |
| 6,057,155 | A | 5/2000 | Wickham et al. |
| 6,100,086 | A | 8/2000 | Kaplan et al. |
| 6,127,525 | A | 10/2000 | Crystal et al. |
| 6,287,857 | B1 | 9/2001 | O'riordan et al. |
| 6,306,652 | B1 | 10/2001 | Fallaux et al. |
| 6,486,133 | B1 | 11/2002 | Herlyn et al. |
| 6,492,169 | B1 | 12/2002 | Vogels et al. |

FOREIGN PATENT DOCUMENTS

| | | |
|---|---|---|
| EP | 1 020 529 A2 | 7/2000 |
| EP | 1 067 188 A1 | 1/2001 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/15644 | 7/1994 |
| WO | WO 94/17832 | 8/1994 |
| WO | WO 94/24299 | 10/1994 |
| WO | WO 94/26915 | 11/1994 |
| WO | WO 95/05201 | 2/1995 |
| WO | WO 95/06745 | 3/1995 |
| WO | WO 95/14785 | 6/1995 |
| WO | WO 95/16037 | 6/1995 |
| WO | WO 95/21259 | 8/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 96/00326 | 1/1996 |
| WO | WO 96/00790 | 1/1996 |
| WO | WO 96/07739 | 3/1996 |
| WO | WO 96/10087 | 4/1996 |
| WO | WO 96/12030 | 4/1996 |
| WO | WO 96/13597 | 5/1996 |
| WO | WO 96/13598 | 5/1996 |
| WO | WO 96/14837 | 5/1996 |
| WO | WO 96/17073 | 6/1996 |
| WO | WO 96/ 18740 | 6/1996 |
| WO | WO 96/24453 | 8/1996 |
| WO | WO 96/26281 | 8/1996 |
| WO | WO 96/35798 | 11/1996 |
| WO | WO 97/00326 | 1/1997 |
| WO | WO 97/12986 | 4/1997 |
| WO | WO 97/20575 A1 | 6/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/22609 | 5/1998 |
| WO | WO 98/ 32842 | 7/1998 |
| WO | WO 98/40509 | 9/1998 |
| WO | WO 98/49300 | 11/1998 |
| WO | WO 98/50053 A1 | 11/1998 |
| WO | WO 99/32647 | 7/1999 |
| WO | WO 99/47180 A1 | 9/1999 |
| WO | WO 99/55132 | 11/1999 |
| WO | WO 99/58646 | 11/1999 |
| WO | WO 00/03029 | 1/2000 |
| WO | WO 00/24730 A2 | 5/2000 |
| WO | WO 00/31285 A1 | 6/2000 |
| WO | WO 00/52186 | 9/2000 |
| WO | WO 00/70071 A1 | 11/2000 |
| WO | WO 01/04334 A2 | 1/2001 |
| WO | WO 01/90158 A1 | 11/2001 |
| WO | WO 02/24730 | 3/2002 |
| WO | WO 02/27006 A1 | 4/2002 |

OTHER PUBLICATIONS

Khurana, et al. (2001) Hypertension, 38: 1210-16.*
Schiavone, et al. (2004) Curr. Pharm. Des., 10: 769-84.*
Bouri, et al. (1999) Hum. Gene Therapy, 10(12): 1633-40.*
Kypson, et al. (1999) Gene Therapy, 6: 1298-1304.*
Tsukamoto, et al. (1999) Gene Therapy, 6: 1331-35.*
Moisset, et al. (1998) Gene Therapy, 5: 1340-46.*
Abrahamsen et al., "Construction of an Adenovirus Type 7a EIA Vector," Journal of Virology, Nov. 1997, p. 8946-8951 vol. 71, No. 11.
Albiges-Rizo et al., "Human Adenovirus Serotype 3 Fiber Protein," Journal of Biological Chemistry, 266(6), 3961-3967 (1991).
Anderson, Nature, "Human gene therapy," Apr. 1998, vol. 392, pp. 25-30.
Athappilly et al., "The Refined Crystal Structure of Hexon, the Major Coat Protein of Adenovirus Type 2, at 2•9 A Resolution," J. Mol. Biol. (1994) 242, 430-455.
Bai et al., "Mutations That Alter an Arg-Gly-Asp (RGD) Sequence in the Adenovirus Type 2 Penton Base Protein Abolish Its Cell-Rounding Activity and Delay Virus Reproduction in Flat Cells," Journal of Virology, 67(9), 5198-5205 (1993).
Bailey et al., "Phylogenetic Relationships among Adenovirus Serotypes," Virology, 205, 439-452 (1994).
Ball-Goodrich et al., "Parvoviral Target Cell Specificity: Acquisition of Fibrotropism by a Mutant of the Lymphotropic Strain of Minute Virus of Mice Involves Multiple Amino Acid Substitutions within the Capsid," Virology, 184, 175-186 (1991).
Basler et al., Sequence of the immunoregulatory early region 3 and flanking sequences of adenovirus type 35, 1996, Gene 170:249-254.
Basler et al., "Subgroup B Adenovirus Type 35 Early Region 3 mRNAs Differ from Those of the Subgroup C Adenoviruses," VIROLOGY, 215, 165-177 (1996).
Batra et al., "Receptor-mediated gene delivery employing lectin-binding specificity," Gene Therapy, 1, 255-260 (1994).
Berendsen, Herman J.C., A Glimpse of the Holy Grail, Science, 1998, vol. 282, pp. 642-643.
Boursnell et al., "In vitro construction of a recombinant adenovirus Ad2:Ad5," Gene, 13, 311-317 (1981).
Bridge et al., "Adenovirus Early Region 4 and Viral DNA Synthesis," Virology 193, 794-801 (1993).
Brody et al., "Adenovirus-Mediated in Vivo Gene Transfer," Annals New York Academy of Sciences pp. 90-100.
Caillet-Boudin et al., "Functional and Structural Effects of an Ala to Val Mutation in the Adenovirus Serotype 2 Fibre," J. Mol. Biol., 217,477-486 (1991).
Chiu et al., Folding & Design, "Optimizing energy potentials for success in protein tertiary structure prediction," May 1998, 3:223-228.
Chroboczek et al., "The Sequence of the Genome of Adenovirus Type 5 and Its Comparison with the Genome of Adenovirus Type 2," Virology, 186, 280-285 (1992).
Chroboczek et al., Adenovirus Fiber, Current Topics in Microbiology and Immunology 1995;199 (Pt 1) pp. 163-200.
Chu et al., "Cell targeting with retroviral vector particles containing antibodyBenvelope fusion proteins," Gene Therapy, 1, 292-299 (1994).

Cotten et al., "TransferrinBpolycation-mediated introduction of DNA into human leukemic cells: Stimulation by agents that affect the survival of transfected DNA or modulate transferrin receptor levels," Proc. Natl. Acad. Sci. USA, 87, 4033-4037 (1990).

Cotten et al., "High-efficiency receptor-mediated delivery of small and large (48 kilobase gene constructs using the endosome-disruption activity of defective or chemically inactivated adenovirus particles," Proc. Natl. Acad. Sci. USA, 89, 6094-6098 (1992).

Crawford-Miksza et al., "Adenovirus Serotype Evolution Is Driven by Illegitimate Recombination in the Hypervariable Regions of the Hexon Protein," Virology, 224, 357-367 (1996).

Crawford-Miksza et al., "Analysis of 15 Adenovirus Hexon Proteins Reveals the Location and Structure of Seven Hypervariable Regions Containing Serotype-Specific Residues," Journal of Virology, Mar. 1996, p. 1836-1844.

Crompton et al., "Expression of a foreign epitope on the surface of the adenovirus hexon," J. Gen. Virol., 75(1), 133-139 (1994).

Crystal, Ronald, G., "Transfer of Genes to Humans: Early Lessons and Obstacles to Success," Science, 270, 404-410 (1995).

Curiel et al., "High-Efficiency Gene Transfer Mediated by Adenovirus Coupled to DNABPolylysine Complexes," Human Gene Therapy, 3, 147-154 (1992).

Curiel et al., "Adenovirus enhancement of transferrinBpolylysine-mediated gene delivery," Proc. Natl. Acad. Sci. USA, 88, 8850-8854 (1991).

De Jong et al., "Adenovirus Isolates From Urine of Patients with Acquired Immunodeficiency Syndrome," The Lancet, Jun. 11, 1983 pp. 1293-1296.

De Jong et al., Adenoviruses from Human Immunodeficiency Virus-Infected Individuals, Including Two Strains That Represent New Candidate Serotypes Ad50 and Ad51 of Species B1 and D, Respectively, Journal of Clinical Microbiology, Dec. 1999, p. 3940-45, vol. 37, No. 12, American Society for Microbiology.

Defer et al., "Human Adenovirus-Host Cell Interactions: Comparative Study with Members of Subgroups B and C," Journal of Virology, 64(8), 3661-3673 (1990).

Deonarain, "Ligand-targeted receptor-mediated vectors for gene delivery," (1998) Expert Opin. Ther. Pat. 8: 53-69.

Dijkema et al., "Transformation of Primary Rat Kidney Cells by DNA Fragments of Weakly Oncogenic Adenoviruses," Journal of Virology, Dec. 1979, p. 943-950.

Douglas J T et al.: "Strategies to accomplish targeted gene delivery to muscle cells employing tropism-modified adenoviral vectors" Neuromusclar Disorders, Pergamon Press, GB, vol 7, Jul 1997, pp. 284-298, XP002079944 ISSN: 0960-8966.

Dupuit et al., "Regenerating Cells in Human Airway Surface Epithelium Represent Preferential Targets for Recombinant Adenovirus," Human Gene Therapy, 6, 1185-1193 (1995).

Eck et al., "Gene-Based Therapy," (1996) Goodman & Gillman's The Pharmacological Basis of Therapeutics, Mc-Graw-Hill, New York, N. Y., pp. 77-101.

Etienne-Julan et al., "The efficiency of cell targeting by recombinant retroviruses depends on the nature of the receptor and the composition of the artificial cellBvirus linker," Journal of General Virology, 73, 3251-3255 (1992).

Falgout et al., "Characterization of Adenovirus Particles Made by Deletion Mutants Lacking the Fiber Gene," Journal of Virology, 62(2), 622-625 (1988).

Flomenberg et al., "Molecular Epidemiology of Adenovirus Type 35 Infections in Immunocompromised Hosts," The Journal Of Infectious Diseases vol. 155, No. 6, Jun. 1987.

Francki et al., "Classification and Nomenclature of Viruses," Fifth Report of the International Committee on Taxonomy of Viruses; Virology Division of the International Union of Microbiology Societies pp. 140-143.

Gall et al., "Construction and characterization of Hexon-Chimeric Adenoviruses: Specification of adenovirus serotype," 72(12) Journal of Virology 10260-64 (1998).

Gall et al., "Adenovirus Type 5 and 7 Capsid Chimera: Fiber Replacement Alters Receptor Tropism without Affecting Primary Immune Neutralization Epitopes," Journal Of Virology, Apr. 1996, p. 2116-2123.

George et al., "Gene therapy progress and prospects: adenoviral vectors,"Gene Therapy (2003) 10, 1135-1141.

Gorecki, "Prospects and problems of gene therapy: an update," (2001) Expert Opin. Emerging Drugs 6(2): 187-98.

Greber et al., "Stepwise Dismantling of Adenovirus 2 during Entry into Cells," Cell, 75, 477-486 (1993).

Green et al., "Evidence for a repeating cross- sheet structure in the adenovirus fibre," EMBO Journal, 2(8), 1357-1365 (1983).

Grubb et al., Inefficient gene transfer by adenovirus vector to cystic fibrosis airway epithelia of mice and humans, Nature, 371, 802-806 (1994).

Gurunathan et al., American Association of Immunologists, "CD40 Ligand/Trimer DNA Enhances Both Humoral and Cellular Immune Responses and Indicates Protective Immunity to Infectious and Tumor Challenge," 1998, 161:4563-4571.

Han et al., "Ligand-directed retroviral targeting of human breast cancer cells," Proc. Natl. Acad. Sci. USA, 92, 9747-9751 (1995).

He et al., "A simplified system for generating recombinant adenoviruses," Proc. Natl. Acad. Sci. USA vol. 95, pp. 2509-2514, Mar. 1998.

Henry et al., "Characterization of the Knob Domain of the Adenovirus Type 5 Fiber Protein Expressed in *Escherichia coli*," Journal of Virology, 68(8), 5239-5246 (1994).

Hidaka, Chisa, et al., "CAR-dependent and CAR-independent pathways of adenovirus vector-mediated gene transfer and expression in human fibroblasts," 103(4) The Journal of Clinical Investigation 579-87 (Feb. 1999).

Hierholzer et al., "Adenoviruses from Patients with AIDS: A Plethora of Serotypes and A Description of Five New Serotypes of Subgenus D (Types 43-47)," The Journal Of Infectious Diseases vol. 158, No. 4 Oct. 1988.

Hong et al., "The Amino Terminus of the Adenovirus Fiber Protein Encodes the Nuclear Localization Signal," Virology, 185(2), 758-767 (1991).

Horvath et al., "Nonpermissivity of Human Peripheral Blood Lymphocytes to Adenovirus Type 2 Infection, " Journal of Virology, 62(1), 341-345 (1988).

Huang et al., "Upregulation of Integrins $\gamma3$ and $\gamma5$ on Human Monocytes and T Lymphocytes Facilitates Adenovirus-Mediated Gene Delivery," Journal of Virology, 69(4), 2257-2263 (1995).

Imler et al., "Novel complementation cell lines derived from human lung carcinoma A549 cells support the growth of E1-deleted adenovirus vectors," Gene Therapy, vol. 3: p. 75-84, 1996.

Jolly; viral vector systems for gene therapy, 1994, Cancer Gene Therapy, vol. 1, No. 1: 51-64.

Kang et al., "Molecular Cloning And Physical Mapping Of The Dna Of Human Adenovirus Type 35," Acta Microbiologica Hungarica 36 (1), pp. 67-75 (1989).

Kang et al., "Relationship Of E1 And E3 Regions Of Human Adenovirus 35 To Those Of Human Adenovirus Subgroups A, C And D," Acta Microbiologica Hungarica 36 (4), pp. 445-457 (1989).

Karayan et al., "Oligomerization of Recombinant Penton Base of Adenovirus Type 2 and Its Assembly with Fiber in Baculovirus-Infected Cells," Virology, 202, 782-795 (1994).

Kass-Eisler et al., "Quantitative determination of adenovirus-mediated gene delivery to rat cardiac myocytes in vitro and in vivo," Proc. Natl. Acad. Sci. USA, 90, 11498-11502 (1993).

Kmiec, "Gene Therapy," American Scientist, vol. 87, pp. 240.

Komoriya et al., The Minimal Essential Sequence for a Major Cell Type-specific Adhesion Site (CSI) within the Alternatively Spliced Type III Connecting Segment Domain of Fibronectin Is Leucine-Aspartic Acid-Valine,: Journal of Biological Chemistry, 266(23), 15075-15079 (1991).

Krasnykh et al.: "Generation Of Recombinant Adenovirus Vectors With Modified Fibers For Altering Viral Tropism" Journal Of Virology, The American Society For Microbiology, US, vol. 70, No. 10, Oct. 1, 1996, pp. 6839-6846, XP002067518 ISSN: 0022-538X.

Lattanzi, Laura, et al., "High Efficiency Myogenic Conversion of Human Fibroblasts by Adenoviral Vector-mediated *MyoD* Gene Transfer," 101(10) J. Clin. Invest. 2119-28 (May 1998).

Lee et al., "The constitutive expression of the immunomodulatory gp 19k protein in E1⁻, E3⁻ adenoviral vectors strongly reduces the host cytotoxic T cell response against the vector," Gene Therapy (1995) 2, 256-262.

Levrero et al., "Defective and nondefective adenovirus vectors for expressing foreign genes in vitro and in vivo," Gene, 101 (1991) 195-202.

Li et al., "Genetic Relationship between Thirteen Genome Types of Adenovirus 11, 34, and 35 with Different Tropisms," Intervirology 1991;32:338-350.

Liu et al., Molecular Basis of the inflammatory response to adenovirus vectors. Gene Therapy (Oct 2003, 935-40.

Maraveyas et al., "Targeted Immunotherapy B An update with special emphasis on ovarian cancer," Acta Oncologica, 32(7/8), 741-746 (1993).

Mastrangeli et al., "ASero-Switch@ Adenovirus-Mediated In Vivo Gene Transfer: Circumvention of Anti-Adenovirus Humoral Immune Defenses Against Repeat Adenovirus Vector Administration by Changing the Adenovirus Serotype," Human Gene Therapy, 7, 79-87 (1996).

Mathias et al., "Multiple Adenovirus Serotypes Use v Integrins for Infection," Journal of Virology, 68(10), 6811-6814 (1994).

Mautner et al., "Recombination in Adenovirus: DNA Sequence Analysis of Crossover Sites in Intertypic Recombinants," Virology, 131, 1-10 (1983).

Mautner et al., "Recombination in Adenovirus: Analysis of Crossover Sites in Intertypic Overlap Recombinants," Virology, 139, 43-52, (1984).

Merriam-Webster Dictionary (on line) retrieved from the internet<URL:htpp://www.m-w.com/egi-bin/dictionary, "derive," 2002.

Michael et al., "Addition of a short peptide ligand to the adenovirus fiber protein," Gene Therapy, 2, 660-668 (1995).

Michael et al., "Binding-incompetent Adenovirus Facilitates Molecular Conjugate-mediated Gene Transfer by the Receptor-mediated Endocytosis Pathway," Journal of Biological Chemistry, 268(10), 6866-6869 (1993).

Miller et al., "Targeted vectors for gene therapy," FASEB Journal, 9, 190-199 (1995).

Neda et al., "Chemical Modification of an Ecotropic Murine Leukemia Virus Results in Redirection of Its Target Cell Specificity," Journal of Biological Chemistry, 266(22), 14143-14146 (1991).

Nemerow et al., "The Role of v Integrins in Adenovirus Infection," Biology of Vitronectins and their Receptors, 177-184 (1993).

Nemerow et al., "Adenovirus entry into host cells: a role for v integrins," Trends In Cell Biology, 4, 52-55 (1994).

Ngo et al., The Protein Folding Problem and Tertiary Structure Prediction, "Computational Complexity, Protein Structure Prediction, and the Levinthal Paradox," 1994, Merz et al. (Editors), Birkhauser, Boston, MA, pp. 433 and 492-495.

Novelli et al., "Deletion Analysis of Functional Domains in Baculovirus-Expressed Adenovirus Type 2 Fiber," Virology, 185, 365-376 (1991).

Orkin et al., "Report and Recommendations of the Panel to Assess the NIH Investment in Research on Gene Therapy," (1995), file:/// F/N1Hrec.htm ¼/01 1:37 pm.

Peteranderl et al., "Trimerization of the Heat Shock Transcription Factor by a Triple-Stranded -Helical Coiled-Coil," Biochemistry, 31, 12272-12276 (1992).

Prince, "Gene transfer: A Review Of Methods And Applications," Pathology (1998), 30, pp. 335-347.

Pring-Åkerblom et al., "Sequence Characterization and Comparison of Human Adenovirus Subgenus B and E Hexons," Virology, 212, 232-36 (1995).

Ragot et al.,: "Efficient adenovirus-mediated transfer of a human minidystrophin gene to skeletal muscle of mdx mice" Nature, Macmillan Journals Ltd. London, GB, vol. 361, No. 6413, 1993, pp. 647-650, XP002162515 ISSN: 0028-0836.

Rea et al., "Highly efficient transduction of human monocyte-derived dendritic cells with subgroup B fiber-modified adenovirus vectors enhances transgene-encoded antigen presentation to cytotoxic T cells," Journal Of Immunology, (Apr. 15, 2000) 166 (8) 5236-44.,—Apr. 15, 2001 XP002192775.

Robbins et al., "Viral Vectors for Gene Therapy," Pharmacol. Ther. vol. 80, No. 1, pp. 35-47, 1998.

Roberts et al., "Three-Dimensional Structure of the Adenovirus Major Coat Protein Hexon," Science, 232, 1148-51 (1986).

Roelvink et al., The Coxsackievirus-Adenovirus Receptor Protein Can Function as a Cellular Attachment Protein for Adenovirus Serotypes from Subgroups A, C, D, E, and F, Journal Of Virology, Oct. 1998, p. 7909-7915, vol. 72, No. 10.

Romano, "Gene Transfer in Experimental Medicine," Drug & News Perspectives, vol. 16, No. 5, 2003, 13 pages.

Russell et al., "Retroviral vectors displaying functional antibody fragments," Nucleic Acids Research, 21(5), 1081-1085 (1993).

Russell, "Replicating Vectors for Gene Therapy of Cancer: Risks, Limitations and Prospects," European Journal of Cancer, vol. 30A, No. 8, pp. 1165.

Sabourin et al., "The molecular regulation of myogenesis," (2000) Clin. Genet. 57(1): 16-25.

Schnurr et al., "Two New Candidate Adenovirus Serotypes," Intervirology 1993;36:79-83.

Schulick et al., "Established Immunity Precludes Adenovirus-mediated Gene Transfer in Rat Carotid Arteries," The Journal of Clinical Investigation vol. 99, No. 2, Jan. 1997, 209-219.

Segerman et al.: "Adenovirus types 11p and 35p show high binding efficiencies for committed hematopoietic cell lines and are infective to these cell lines" Journal of Virology, The American Society for Microbiology, US, vol. 74, No. 3, Feb. 2000 (200-02), pp. 1457-1467, XP002161682 ISSN: 0022-538X.

Shayakhmetov et al., "Efficient Gene Transfer into Human CD34⁺Cells by a Retargeted Adenovirus Vector," Journal Of Virology, Mar. 2000, p. 2567-2583.

Signäs et al., "Adenovirus 3 Fiber Polypeptide Gene: Implications for the Structure of the Fiber Protein," Journal of Virology, 53(2), 672-678 (1985).

Silver et al., "Interaction of Human Adenovirus Serotype 2 with Human Lymphoid Cells," Virology, 165, 377-387 (1988).

Stevenson et al.; Selective Targeting of Human Cells by a Chimeric Adenovirus Vector Containing a Modified Fiber Protein, 1997, Journal of Virology, vol. 71: 4782-4790.

Stewart et al., "Difference imaging of adenovirus: bridging the resolution gap between X-ray crystallography and electron microscopy," EMBO Journal, 12(7), 2589-2599 (1993).

Stratford-Perricaudet LD et al.: "Widespread Long-Term Gene Transfer To Mouse Skeletal Muscles And Heart" Journal Of Clinical Investigation, New York, NY, US, vol. 90 No. 2, Aug. 1992, ISSN: 0021-9738.

Toogood et al., "The Adenovirus Type 40 Hexon: Sequence, Predicated Structure and Relationship to Other Adenovirus Hexons," J. gen. Virol (1989), 70, 3203-3214.

Valderrama-Leon et al., "Restriction Endonuclease Mapping of Adenovirus 35, a Type Isolated from Immunocompromised Hosts," Journal Of Virology, Nov. 1985, p. 647-650.

Verma et al., Nature, "Gene therapy-promises, problems and prospects," Sep. 1997, vol. 389, pp. 239-242.

Wadell, "Molecular Epidemiology of Human Adenoviruses," Microbiology and Immunology, vol. 110 pp. 191-220.

Wagner et al., "Coupling of adenovirus to transferrinBpolylysine/DNA complexes greatly enhances receptor-mediated gene delivery and expression of transfected genes," Proc. Natl. Acad. Sci. USA, 89, 6099-6103 (1992).

Watson et al., "An Antigenic Analysis of the Adenovirus Type 2 Fibre Polypeptide," Journal of Virology, 69, 525-535 (1988).

Wickham et al., "Integrins $_{v3}$ and $_{v5}$ Promote Adenovirus Internalization but Not Virus Attachment," Cell, 73, 309-319 (1993).

Wickham et al., "Integrin γ5 Selectively Promotes Adenovirus Mediated Cell Membrane Permeabilization," Journal of Cell Biology, 127(1), 257-264 (1994).

Wickham et al.: "Increased In Vitro and In Vivo Gene Transfer by Adenovirus Vectors Containing Chimeric Fiber Proteins," Journal of Virology, Nov. 1997, p. 8221-8229.

Zhong et al.: "Recombinant Advenovirus Is An Efficient And Non-Pertubing Genetic Vector For Human Dendritic Cells" European Journal Of Immunology, Weinheim, DE, vol. 29, No. 3, 1999, pp. 964-972, XP000938797 ISSN: 0014-2980.

Flomenberg et al., "Sequence and genetic Organization of Adenovirus Type 35 Early Region 3," Journal of Virology, Nov. 1988, pp. 4431-4437, vol. 62, No. 11.□.

Gahery-Segard et al., "Immune response to recombinant Capsid Proteins of Adenovirus in Humans: Antifiber and Anti-Penton Base Antibodies Have a Synergistic Effect on Neutralizing Activity," Journal of Virology, Mar. 1998, pp. 2388-2397, vol. 72, No. 3.

Rosenfeld et al., Adenovirus-Mediated Transfer of a recombinant alpha-1-Antitrypsin Gene to the Lung Epithelium in Vivo, Science, Apr. 19, 1991, pp. 431-434, vol. 252.

Roy et al., "Circumvention of Immunity to the Adenovirus major Coat Protein Hexon," Journal of Virology, Aug. 1998, pp. 6875-6879, vol. 72, No. 8.

Stevenson et al., "Human Adenovirus Serotypes 3 and 5 Bind to Two Different Cellular receptors via the Fiber Head Domain," Journal of Virology, May 1995, pp. 2850-2857, vol. 69, No. 5.

Stratford-Perricaudet et al., "Evaluation of the Transfer and Expression in Mice of an Enzyme-Encoding Gene Using a Human Adenovirus Vector," Human Gene Therapy, 1990, pp. 241-256, vol. 1.

Akkaraju et al., "Herpes simplex virus vector-mediated dystrophin gene transfer and expression in MDX mouse skeletal muscle," J Gene Med, Jul.-Aug. 1999, pp. 280-289, vol. 1, No. 4. Abstract.

Arnberg et al., "Fiber genes of adenoviruses with tropism for the eye and the genital tract," Virology, Jan. 6, 1997, pp. 239-244, vol. 227, No. 1. Abstract.

Blaese et al., "Vectors in cancer therapy: how will they deliver?" Cancer Gene Therapy, 1995, pp. 291-297, vol. 2, No. 4.

Bordet et al., "Adenoviral cardiotrophin-1 gene transfer protects pmn mice from progressive motor neuronopathy," J. Clin. Invest., Oct. 1999, pp. 1077-1085, vol. 104, No. 8.

Bout, A., "Prospects for human gene therapy,"Eur J Drug Metab Pharmacokinet, Apr.-Jun. 1996, pp. 175-179, vol. 21, No. 2. Abstract.

Brody et al., "Adenovirus-Mediated in Vivo Gene Transfer," Annals New York Academy of Sciences, 1994, pp. 90-101, vol. 716.

Chao et al., "Persistent expression of canine factor 1X in hemophilia B canines," Gene Ther., Oct. 1999, pp. 1695-1704, vol. 6, No. 10. Abstract.

Dalle et al., "Improvement of mouse beta-thalassemia upon erythropoietin delivery by encapsulated myoblsast," Gene Ther, Feb. 1999, pp. 157-161, vol. 6, No. 2. Abstract.

Diedwardo et al., "Muscle tissue engineering," Clin Plast Surg, Oct. 1999, pp. 647-656, vol. 26, No. 4. Abstract.

Dimauro et al., "Glycogen storage disease of muscle," Curr Opin Neurol, Oct. 1998, pp. 477-484, vol. 11, No. 5. Abstract.

Goncalves et al., "Prolonged Transgene Expression Provided by a High-capacity Adeno-associated Virus/Adenovirus Hybrid Vector," Molecular Therapy, 2000, pp. S137, vol. 1, No. 5. Abstract 351.

Hartigan-O'Connor et al., "Developments in gene therapy for muscular dystrophy," Microsc Res Tech, Feb. 1-15, 2000, pp. 223-238, vol. 48, No. 3-4. Abstract.

Hierholzer et al., "Adenoviruses from Patients with AIDS: A plethora of Serotypes and A Description of Five New Serotypes of Subgenus D (Types 43-47)," J Infect Dis, Oct. 1988, pp. 804-813, vol. 158, No. 4. Abstract.

Hynes et al., "Integrins: Versatility, Modulation, and Signaling in Cell Adhesion," Cell, Apr. 3, 1992, pp. 11-25, vol. 69.

Ishibashi et al., "The Adenoviruses," H.S. Ginsberg ed., 1984, Chapter 12, pp. 497-561.

Isner et al., "Angiogenesis: a "breakthrough" technology in cardiovascular medicine," J Invasive Cardiol., Feb. 2000, pp. 14A-17A, vol. 12 Suppl A. Abstract.

Jackson et al., "Hematopoietic potential of stem cells isolated from murine skeletal muscle," Proc Natl Acad Sci, Dec. 7, 1999, pp. 14482-14486, vol. 96, No. 25.

Jaffe et al., "Culture of Human Endothelial Cells Derived from Umbilical Veins," J Clin Invest., Nov. 1973, pp. 2745-2756, vol. 52.

Kay et al., "Expression cloning of a c DNA encoding M1/69-J11d heat-stable antigens," J Immunol, Sep. 15, 1990, pp. 1952-1959, vol. 145, No. 6. Abstract.

Khoo et al., "Adenovirus infections in human immunodeficiency virus-positive patients: clinical features and molecular epidemiology," J Infect Dis, Sep. 1995, pp. 629-637, vol. 172, No. 3. Abstract.

Kidd et al., "Adenovirus type 40 virions contain two distinct fibers," Virology, Jan 1993, pp. 73-84, vol. 192, No. 1. Abstract.

Li et al., "Dose control with cell lines used for encapsulated cell therapy," Tissue Eng, Oct. 1999, pp. 453-466, vol. 5, No. 5. Abstract.

Li, R., "Materials for immunoisolated cell transplantation," Adv Drug Delivery Rev, Aug. 3, 1998, pp. 87-109, vol. 33, No. 1-2. Abstract.

Li et al., "Increased level and duration of expression in muscle by co-expression of a transactivator using plasmid systems," Gene Ther, Dec. 1999, pp. 2005-2011, vol. 6, No. 12. Abstract.

Maccoll et al., "Using skeletal muscle as an artificial endocrine tissue," J Endocrin, 1999, pp. 1-9, vol. 162.

Mohajeri et al., "Intramuscular grafts of myoblasts genetically modified to secrete glial cell line-derived neurotrophic factor prevent motoneuron loss and disease progression in a mouse model of familial amyotrophic lateral sclerosis," Hum Gene Ther, Jul. 20, 1999, pp. 1853-1866, vol. 10, No. 11. Abstract.

Morgan et al., "Structure and Development of Viruses as Observed in the Electron Microscope, X. Entry and Uncoating of Adenovirus," Journal of Virology, Nov. 1969, pp. 777-796, vol. 4, No. 5.

Morino et al., "Hammerhead ribozyme specifically inhibits vascular endothelial growth factor gene expression in a human hepatocellular carcinoma cell line," Int J Oncol, Sep. 2000, pp. 495-499, vol. 17, No. 3. Abstract.

Moullier et al., "Continuous systemic secretion of a lysosomal enzyme by genetically modified mouse skin fibroblasts," Transplantation, Aug. 1993, pp. 427-432, vol. 56, No. 2. Abstract.

Powell et al., "Tissue-engineered human bioartifical muscles expressing a foreign recombinant protein for gene therapy," Hum Gene Ther, Mar. 1, 1999, pp. 565-577, vol. 10, No. 4. Abstract.

Quax et al., "Binding of Human Urokinase-Type Plasminogen Activator to Its Receptor, Residues Involved in Species Specificity and Binding," Arteriocler Thromb Vasc Biol, May 1998, pp. 693-701, vol. 18.

Rando et al., "Rescue of dystrophin expression in mdx mouse muscle by RNA/DNA oligonucleotides," Pro Natl Acad Sci, May. 9, 2000. pp. 5363-5368, vol. 97, No. 10.

Regulier et al., "Continuous delivery of human and mouse erythropoietin in mice by genetically engineered polymer encapsulated myoblasts," Gene Ther, Aug. 1998, pp. 1014-1022, vol. 5, No. 8. Abstract.

Rivard et al., "Rescue of Diabetes-Related Impairment of Angiogenesis by Intramuscular Gene Therapy with Adeno-VEGF," American Journal of Pathology, Feb. 1999, pp. 355-363, vol. 154, No. 2.

Rosenthal et al., "Collagen as a matrix for neo-organ formation by gene-transfected fibroblasts," Anticancer Res, Mar.-Apr. 1997, pp. 1179-1186, vol. 17, No. 2A. Abstract.

Schnurr et al., "Two new candidate adenovirus serotypes," Intervirology, 1993, pp. 79-83, vol. 36, No. 2.

Schratzberger et al., "Favorable effect VEGF gene transfer on ischemic peripheral neuropathy," Nat Med, Apr. 2000, pp. 405-413, vol. 6, No. 4. Abstract.

Scorsin et al., "Comparison of the effects of fetal cardiomyocyte and skeletal myoblast transplantation on postinfarction left ventricular function," J Thorac Cardiovasc Surg, Jun. 2000, pp. 1169-1175, vol. 119, No. 6. Abstract.

Soreq et al., "Anti-sense approach to anticholinesterase therapeutics," Isr Med Assoc J, Jul 2000, pp. 81-85, vol. 2 suppl. Abstract.

Stouten et al., "New triple-helical model for the shaft of the adenovirus fibre," J Mol Biol, Aug. 20, 1992, pp. 1073-1084, vol. 224, No. 4. Abstract.

Svensson et al., "Entry of Adenovirus 2 into HeLa Cells," Journal of Virology, Sep. 1984, pp. 687-694, vol. 51, No. 3.

Ueno et al., "A soluble transforming growth factor beta receptor expressed in muscle prevents liver fibrogenesis and dysfunction in rats," Hum Gene Ther, Jan. 1, 2000, pp. 33-42, vol. 11, No. 1. Abstract.

Varga et al., "Infectious Entry Pathway of Adenovirus Type 2," Journal of Virology, No. 1991, pp. 6061-6070, vol. 65, No. 11.

Vilquin et al., "Myoblast transplantations lead to the expression of the laminin alpha 2 chain in normal and dystrophic (dy/dy) mouse muscles," Gene Ther. May 1999, pp. 792-800, vol. 6, No. 5. Abstract.

Wickham et al., "Targeting of Adenovirus penton base to new receptors through replacement of its RGD motif with other receptor-specific peptide motifs," gene Ther, Dec. 1995, pp. 750-756, vol. 2, No. 10. Abstract.

Wunberg et al., "The migration of human smooth muscle cells in vitro is mediated by plasminogen activation and can be inhibited byalpha2-macroglobulin receptor associated protein," Throm Haemost, Aug. 1997, pp. 880-886, vol. 78, No. 2. Abstract.

Yoo et al., "A novel gene delivery system using urothelial tissue engineered neo-organs," J Urol, Sep. 1997, pp. 1066-1070, vol. 158, No. 3 pt 2. Abstract.

Verma et al., Nature "Gene therapy-promises, problems and prospects," Sep. 1997, vol. 389, pp. 239-242.

Wadell, "Molecular Epidemiology of Human Adenoviruses," vol. 110 pp. 191-220. (1984), Current Topics in Microbiology & Immunology.

Russell, "Replicating Vectors for Gene Therapy of Cancer: Risks, Limitations and Prospects," European Journal of Cancer, vol. 30A, No. 8, pp. 1165, (1994).

Kmiec, "Gene Therapy," American Scientist, vol. 87, pp. 240-247, (1999).*

Brody et al., "Adenovirus-Mediated in Vivo Gene Transfer," Annals New York Academy of Sciences pp. 90-100, vol. 716 (1994).

* cited by examiner

SEQUENCE LISTING

<160> NUMBER OF SEQ ID NOS: 14

<210> SEQ ID NO 1
<211> LENGTH: 6
<212> TYPE: PRT
<213> ORGANISM: Adenovirus
<220> FEATURE:
<223> OTHER INFORMATION: Conserved region in adenovirus fiber protein

<400> SEQUENCE: 1

Phe Asn Pro Val Tyr Pro
1               5

<210> SEQ ID NO 2
<211> LENGTH: 23
<212> TYPE: DNA
<213> ORGANISM: Artificial
<220> FEATURE:
<223> OTHER INFORMATION: Synthetic oligonucleotide

<400> SEQUENCE: 2
aattgtctta attaaccgct taa                                           23

<210> SEQ ID NO 3
<211> LENGTH: 19
<212> TYPE: DNA
<213> ORGANISM: Artificial
<220> FEATURE:
<223> OTHER INFORMATION: Synthetic oligonucleotide

<400> SEQUENCE: 3
aattgtctta attaaccgc                                                19

<210> SEQ ID NO 4
<211> LENGTH: 19
<212> TYPE: DNA
<213> ORGANISM: Artificial
<220> FEATURE:
<223> OTHER INFORMATION: Synthetic oligonucleotide

<400> SEQUENCE: 4
aattgcggtt aattaagac                                                19

<210> SEQ ID NO 5
<211> LENGTH: 47
<212> TYPE: DNA
<213> ORGANISM: Artificial
<220> FEATURE:
<223> OTHER INFORMATION: Synthetic oligonucleotide LTR-1

-continued

```
<400> SEQUENCE: 5
ctgtacgtac cagtgcactg gcctaggcat ggaaaaatac ataactg                    47

<210> SEQ ID NO 6
<211> LENGTH: 64
<212> TYPE: DNA
<213> ORGANISM: Artificial
<220> FEATURE:
<223> OTHER INFORMATION: Synthetic oligonucleotide LTR-2

<400> SEQUENCE: 6
gcggatcctt cgaaccatgg taagcttggt accgctagcg ttaaccgggc gactcagtca      60
atcg                                                                  64

<210> SEQ ID NO 7
<211> LENGTH: 28
<212> TYPE: DNA
<213> ORGANISM: Artificial
<220> FEATURE:
<223> OTHER INFORMATION: Synthetic oligonucleotide HSA1

<400> SEQUENCE: 7
gcgccaccat gggcagagcg atggtggc                                        28

<210> SEQ ID NO 8
<211> LENGTH: 50
<212> TYPE: DNA
<213> ORGANISM: Artificial
<220> FEATURE:
<223> OTHER INFORMATION: Synthetic oligonucleotide HSA2

<400> SEQUENCE: 8
gttagatcta agcttgtcga catcgatcta ctaacagtag agatgtagaa                50

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide Primer 1

<400> SEQUENCE: 9
gggtattagg ccaaaggcgc a                                               21

<210> SEQ ID NO 10
<211> LENGTH: 33
<212> TYPE: DNA
<213> ORGANISM: Artificial
<220> FEATURE:
<223> OTHER INFORMATION: Synthetic oligonucleotide Primer 2

<400> SEQUENCE: 10
gatcccatgg aagcttgggt ggcgacccca gcg                                  33

<210> SEQ ID NO 11
<211> LENGTH: 36
<212> TYPE: DNA
<213> ORGANISM: Artificial
<220> FEATURE:
<223> OTHER INFORMATION: Synthetic oligonucleotide Primer 3

<400> SEQUENCE: 11
gatcccatgg ggatccttta ctaagttaca aagcta                               36
```

```
<210> SEQ ID NO 12
<211> LENGTH: 19
<212> TYPE: DNA
<213> ORGANISM: Artificial
<220> FEATURE:
<223> OTHER INFORMATION: Synthetic oligonucleotide Primer 4

<400> SEQUENCE: 12
gtcgctgtag ttggactgg                                              19

<210> SEQ ID NO 13
<211> LENGTH: 42
<212> TYPE: DNA
<213> ORGANISM: Artificial
<220> FEATURE:
<223> OTHER INFORMATION: Synthetic oligonucleotide NY-up

<400> SEQUENCE: 13
cgacatatgt agatgcatta gtttgtgtta tgtttcaacg tg                    42

<210> SEQ ID NO 14
<211> LENGTH: 18
<212> TYPE: DNA
<213> ORGANISM: Artificial
<220> FEATURE:
<223> OTHER INFORMATION: Synthetic oligonucleotide NY-down

<400> SEQUENCE: 14
ggagaccact gccatgtt                                               18
```

SEROTYPE 5 ADENOVIRAL VECTORS WITH CHIMERIC FIBERS FOR GENE DELIVERY IN SKELETAL MUSCLE CELLS OR MYOBLASTS

CROSS-REFERENCE TO RELATED APPLICATIONS

This application is a national entry under 35 U.S.C. § 371 of PCT/NL01/00703, filed Sep. 25, 2001, published in English on Apr. 4, 2002, as WO 02/27006 A1, which claims the benefit of U.S. Provisional Application No. 60/235,665, filed Sep. 26, 2000.

FIELD OF THE INVENTION

The invention relates to the field of molecular genetics and medicine. More in particular the invention relates to adenoviral vectors for targeting to skeletal muscle and/or myoblast cells.

BACKGROUND OF THE INVENTION

The technology of delivering genetic material to cells is currently wide spread and finds many applications. With the technology at hand, it is possible to transfer a wide variety of nucleic acids into a wide variety of different cell types. Some of the more classical technologies include calcium phosphate precipitation, liposome mediated transfer, viral vector mediated transfer, particle bombardment and electroporation.

However, there is no ideal system for the transfer of nucleic acid into cells. All of the transfer systems of the art have their advantages and disadvantages. For instance, the calcium phosphate technology has been shown to be very effective in the transfection of many in vitro growing immortalized cell lines, however, transfer of nucleic acid into many primary cells both in vitro and in vivo has proven to be very difficult. In fact, efficient transfer of nucleic acid in primary cells has only become broadly applicable with the development of systems that use viral elements. Such viral vector systems utilize the very efficient mechanisms that viruses have developed to introduce their genetic information into the target cell. One of the best-studied viral vector systems is the adenovirus vector system.

Gene-transfer vectors derived from adenoviruses (so-called adenoviral vectors) have a number of features that make them particularly useful for gene transfer. 1) the biology of the adenoviruses is characterized in detail, 2) the adenovirus is not associated with severe human pathology, 3) the virus is extremely efficient in introducing its DNA into the host cell, 4) the virus can infect a wide variety of cells and has a broad host-range, 5) the virus can be produced at high virus titers in large quantities, and 6). The virus can be rendered replication defective by deletion of the early-region 1 (E1) of the viral genome (Brody and Crystal 1994).

The adenovirus genome is a linear double-stranded DNA molecule of approximately 36000 base pairs. The adenovirus DNA contains identical Inverted Terminal Repeats (ITR) of approximately 90-140 base pairs with the exact length depending on the serotype. The viral origins of replication are within the ITRs exactly at the genome ends. Most adenoviral vectors currently used in gene therapy have a deletion in the E1 region, where novel genetic information can be introduced. The E1 deletion renders the recombinant virus replication defective. (Levrero et al. 1991). It has been demonstrated extensively that recombinant adenovirus, in particular serotype 5, is suitable for efficient transfer of genes in vivo to the liver, the airway epithelium and solid tumors in animal models and human xenografts in immuno-deficient mice (Bout 1996; Blaese et al. 1995). Thus, preferred methods for in vivo gene transfer into target cells make use of adenoviral vectors as gene delivery vehicles. At present, six different subgroups of human adenoviruses have been proposed which in total encompasses 51 distinct adenovirus serotypes. Besides these human adenoviruses an extensive number of animal adenoviruses have been identified (Ishibashi and Yasue 1984).

A serotype is defined on the basis of its immunological distinctiveness as determined by quantitative neutralization with animal antisera (horse, rabbit). If neutralization shows a certain degree of cross-reaction between two viruses, distinctiveness of serotype is assumed if A) the hemagglutinins are unrelated, as shown by lack of cross-reaction on hemagglutination-inhibition, or B) substantial biophysical/biochemical differences in DNA exist (Francki et al. 1991). The nine serotypes identified last (42-51) were isolated for the first time from HIV-infected patients. (Hierholzer et al. 1988; Schnurr and Dondero 1993; De Jong et al. 1999). For reasons not well understood, most of such immuno-compromised patients shed adenoviruses that were rarely or never isolated from immuno-competent individuals (Hierholzer et al. 1988; Khoo et al. 1995; De Jong et al., 1999). The adenovirus serotype 5 (Ad5), is most widely used for gene therapy purposes. Similar to serotypes 2, 4 and 7, serotype 5 has a natural affiliation towards lung epithelia and other respiratory tissues. In contrast, it is known that, for instance, serotypes 40 and 41 have a natural affiliation towards the gastrointestinal tract. For a detailed overview of the disease association of the different adenovirus serotypes see table 1. In this table there is one deviation from the literature. Sequence analysis and hemagglutination assays using erythrocytes from different species performed in our institute indicated that in contrast to the literature (De Jong et al. 1999) adenovirus 50 proved to be a D group vector whereas adenovirus 51 proved to be a B-group vector. The natural affiliation of a given serotype towards a specific organ can either be due to a difference in the route of infection i.e. make use of different receptor molecules or internalization pathways. However, it can also be due to the fact that a serotype can infect many tissues/organs but it can only replicate in one organ because of the requirement of certain cellular factors for replication and hence clinical disease. At present it is unknown which of the above mentioned mechanisms is responsible for the observed differences in human disease association. However it is known that different adenovirus serotypes can bind to different receptors due to sequence dissimilarity of the capsid proteins i.e. hexon, penton, and fiber protein. It is predominantly fiber that is responsible for the initial attachment and thus determines the host range of a serotype. For instance, it has been shown that adenoviruses of subgroup C such as Ad2 and Ad5 bind to different receptors as compared to adenoviruses from subgroup B such as Ad3 (Defer et al. 1990). Likewise, it was demonstrated that receptor specificity could be altered by exchanging the Ad3 with the Ad5 knob protein, and vice versa (Krasnykh et al. 1996; Stevenson et al. 1995 and 1997).

The initial step for successful infection is binding of adenovirus to a cell surface, a process mediated through fiber protein. The fiber protein has a trimeric structure (Stouten et al. 1992) with different lengths, depending on the virus serotype (Signas et al. 1985; Kidd et al. 1993). Different serotypes have polypeptides with structurally similar N and C termini, but different middle stem regions. N-terminally, the first 30 amino acids are involved in anchoring of the fiber to the penton base (Chroboczek et al. 1995), especially the conserved FNPVYP (SEQ. ID. NO. 1) region in the tail (Arnberg et al. 1997). The C-terminus, or knob, is responsible for initial interaction with the cellular adenovirus receptor. After this initial binding secondary binding between the capsid penton base and cell-surface integrins is proposed to lead to internalization of viral particles in coated pits and endocytosis (Morgan et al. 1969; Svensson and Persson 1984; Varga et al. 1991; Greber et al. 1993; Wickham et al. 1995). Integrins are αβ-heterodimers of which at least 14 α-subunits and 8 β-subunits have been identified (Hynes 1992). The array of integrins expressed in cells is complex and will vary between cell types and cellular environment. Although the knob contains some conserved regions, between serotypes, knob proteins show a high degree of variability, indicating that different adenovirus receptors might exist. For instance, it has been demonstrated that adenoviruses of subgroup C (Ad2, Ad5) and adenoviruses of subgroup B (Ad3) bind to different receptors (Defer et al. 1990). Using baculovirus produced soluble CAR as well as adenovirus serotype 5 knob protein, Roelvink et al. (1998) concluded by using interference studies that all adenovirus serotypes, except serotypes of subgroup B, enter cells via CAR.

Although adenovirus vectors have been used to transfer foreign genetic material into a large variety of cell types, skeletal muscle cells (also referred to as muscle cells) and muscle cell specific precursors thereof (myoblasts) have until the present invention at least in part resisted efficient gene delivery by adenovirus vectors. Until the present invention, the limited capability of adenovirus vectors to deliver a nucleic acid of interest to said (precursor) muscle cell was a problem in gene therapy. Effective gene delivery in said cells is desirable, because in the field of gene therapy there is an interest in skeletal muscle as a target for treatment of many different diseases (reviewed in DiEdwardo et al. 1999). For instance, via direct injection of skeletal muscle with either recombinant viruses (Hartigan-O'Connor and Chamberlain 2000; Akkaraju et al. 1999), naked DNA (Li S. et al. 1999) or liposome complexed DNA, researchers are attempting to treat local muscle disease such as Duchenne muscular dystrophy (DMD). In DMD, proper dystrophin protein expression is impaired due to genetic deletions. However, other structural proteins such as, lamanin-alpha-2-chain, or delta-sarcoglyan cause other types of muscle disease and are therefore also subject of investigation (Vilquin et al. 1999).

Besides muscle diseases, a large number of other human diseases can potentially be treated if highly efficient transduction of skeletal muscle would occur, since skeletal muscle presents a large mass of the human body that is easily accessible. For instance, expression of proteins that are either wrongly expressed, or not expressed at all by a patient suffering from one of many glycogen storage disorders could potentially be treated. Genes known to be non-functional are: for instance Aldolase A, Phosphorylase B-kinase, acid maltase, or ormyophosphorylase (reviewed in DiMauro and Bruno, 1998).

Another example of potential areas in which efficient genetic modification of skeletal muscle could be beneficial are ischemia and peripheral vascular disease because induction of angiogenesis has been shown to be therapeutically beneficial (Isner 2000, Schratzberger et al. 2000). Factors that can induce or inhibit angiogenesis are for instance cardiotropin-1, ang1-7, NOSIII, ATF-BPTI, and vascular endothelial growth factor (Bordet et al. 1999; Rivard et al. 1999). Another example is the genetic modification of the skeletal muscle such that it becomes a "production factory" for therapeutic proteins that can exert their therapeutic effect at sites distant from the skeletal muscle (MacColl et al. 1999). Examples of the latter include growth factors and hormones i.e. EPO, TGF-β, TNF-α, or IL1-IL12 (Ueno et al. 2000; Dalle et al. 1999), blood clotting factors i.e. factor VIII and factor IX (Chao et al. 1999)), neurotropic factors i.e. GDNF or NGF (Mohajeri et al. 1999), or lysosomal lipid degradation enzymes i.e. galactosidase, glucocerebrosidase, ceraminidase. Expression of these proteins in the muscle could be beneficial to treat for instance anemia, blood clotting disorders, or Gaucher disease to name but a few.

Because direct injection of recombinant viruses, naked DNA or liposome complexed DNA has so far not resulted in highly efficient genetic modification of skeletal muscle, alternatives of direct administration approaches are explored. In one such strategy, myoblasts cultured from adult skeletal muscle biopsies are isolated. Myoblasts are subsequently genetically modified and re-infused into the patient, for instance in the skeletal muscle, cardiac muscle or perhaps even in the blood stream giving the fact that, these cells might possess the ability to home to skeletal muscle (Jackson et al. 1999). Transplantation into ischemic regions of a diseased heart of genetically modified myoblasts expressing angiogenic factors might counteract heart failure (Scorsin et al. 2000). This strategy in which genetically modified cells are transplanted directly, is an autologous procedure meaning that cells have to be derived from the patient itself. To broaden the number of applications several polymers have been constructed in which allogeneic cells are encapsulated using semi-permeable membranes which thus shields the cells from the immune system of the host (Li R H. et al. 1998 and 1999). Encapsulated myoblasts thus secrete therapeutic proteins but the myoblasts are protected from the immune system and/or complement inactivation (Regulier et al. 1998; Dalle et al. 1999). Encapsulated cells are surgically implanted at any easy accessible site in the body, i.e. subcutaneous, intra dermal, intra peritoneal, or intra muscular. Another alternative strategy for the direct administration of recombinant viruses, naked DNA, or liposome-complexed DNA is the use of myoblasts for ex vivo tissue engineering also referred to as a "neo-organ approach". This strategy is based on the implantation of cells, either or not genetically modified, in biodegradable scaffolds in vitro (Rosenthal and Kohler 1997, Yoo and Atala 1997, Moullier et al. 1993). The cells adhere to the scaffold after which the scaffold is surgically transplanted. This approach can be used to generate bioartificial muscle (BAM) in bioreactors (Powell et al. 1999). Genes of interest to transfer to myoblasts using this approach are many and include all examples listed so far. Naturally, the same approaches can be followed when undesired genes or proteins have to be eliminated from the body. Hereto, for instance anti-sense molecules (Soreq and Seidman 2000), ribozymes (Morino et al. 20.00), or chimeraplasts (Rando et al. 2000) can be expressed in myoblasts.

From the above non-limiting, examples it can be concluded that efficient transduction of skeletal muscle cells and myoblasts is of great importance. However, although researchers perform a great variety of beneficial applications with gene therapy involving skeletal muscle cells and myoblasts, until the present invention there were no suitable methods for transduction of a skeletal muscle cell and/or a myoblast, a muscle cell specific precursor of at least a skeletal muscle cell.

Transduction of a (precursor) muscle cell with an adenovirus vector was not efficiently possible. Until the present invention, gene delivery was performed in a variety of ways, which were for instance laborious, and/or inefficient. The present invention solves the problem, how a muscle cell and/or a specific precursor thereof can be efficiently infected by a gene delivery vehicle, preferably comprising an adenoviral vector. With the present invention it is for instance possible to perform a wide range of beneficial applications on a wide scale. An efficient way of transducing said (precursor) muscle cells by an adenovirus vector might for instance improve the time and/or extent of treatment of a disease by gene therapy.

BRIEF DESCRIPTION OF THE TABLES AND FIGURES

Table 1: Association of different human adenovirus serotypes with human disease.

Table 2: Production results of recombinant fiber chimaeric adenoviruses. Results in virus particles per milliliter as determined by HPLC. These yields were obtained starting from 9×T175 flask giving full CPE with 2-3 days after virus inoculation.

FIG. 1: Three independent experiments (FIGS. 1A, 1B, and 1C respectively) were performed in which fiber chimaeric vectors were tested for their ability to transduce human A459 lung carcinoma cells. A549 cells were seeded at a density of $10^5$ cells per well of 24-well plates and exposed twenty-four hours after seeding to an increasing dose of virus particles per cells of different fiber chimaeric vectors. The number on the X-axis represents the fiber number (i.e. 16 means Ad5Fib16). The dose of virus particles pier cell used differs between 1A, 1B, and 1C ranging from 10 to 5000 virus particles per cell (dose is indicated on the right). Luciferase activity is expressed in relative light units (RLU) per microgram total cellular protein.

FIG. 2: (A) Fiber chimaeric viruses were tested for their ability to transduce mouse C2C12 myoblasts. The virus dose used of each chimaeric vector was 10, 50, 250, 1250, 2500, and 5000 virus particles per cell. Luciferase activity is expressed in relative light units (RLU) per microgram total cellular protein. (B) Mouse C2C12 myoblasts were cultured to high confluency such that myotube structures are spontaneously formed. The virus dose used of each chimaeric vector is 10, 50, 250, 1250, 2500, and 5000 virus particles per cell. Luciferase activity is expressed in relative light units (RLU) per microgram total cellular protein.

Figure 3:
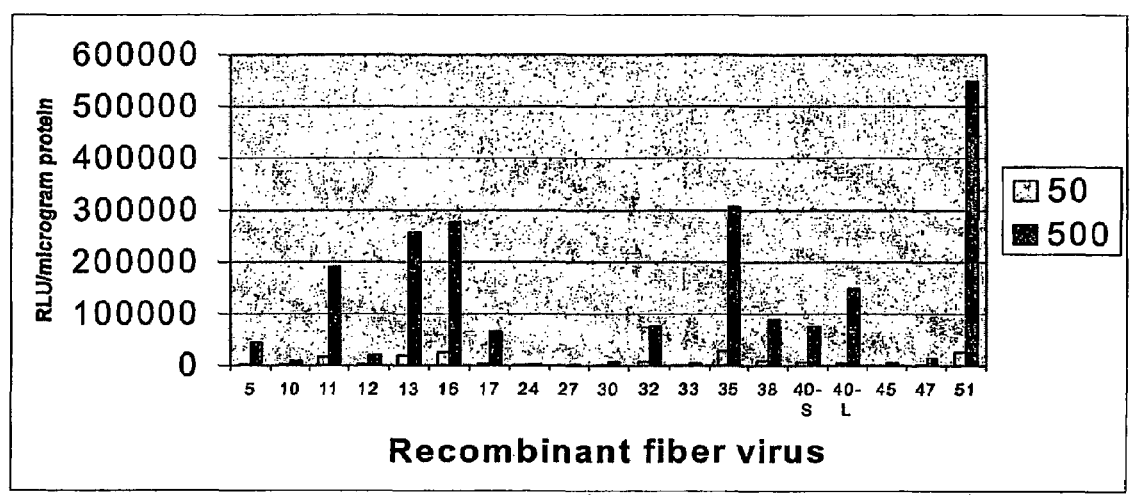

FIG. 3: Fiber chimaeric viruses were tested for their ability to transduce human primary myoblasts. The virus, dose used of each chimaeric fiber virus is 50 or 500 virus particles per cell. Luciferase activity is expressed in relative light units (RLU) per microgram total cellular protein.

FIG. 4: Transduction of human primary myoblasts with fiber chimaeric vectors Ad5Fib16, Ad5Fib35, and Ad5Fib51 carrying green fluorescent protein as a marker gene (GFP). Non-transduced cells were used to set the gate on 1% GFP-positive cells. Values are corrected for background. A) Shown is the percentage of GFP positive cells as determined by flow cytometry forty-eight hours after virus exposure B) Shown is the median fluorescence intensity of the bells which is a parameter that determines how much GFP is produced inside a cell.

Figure 5:
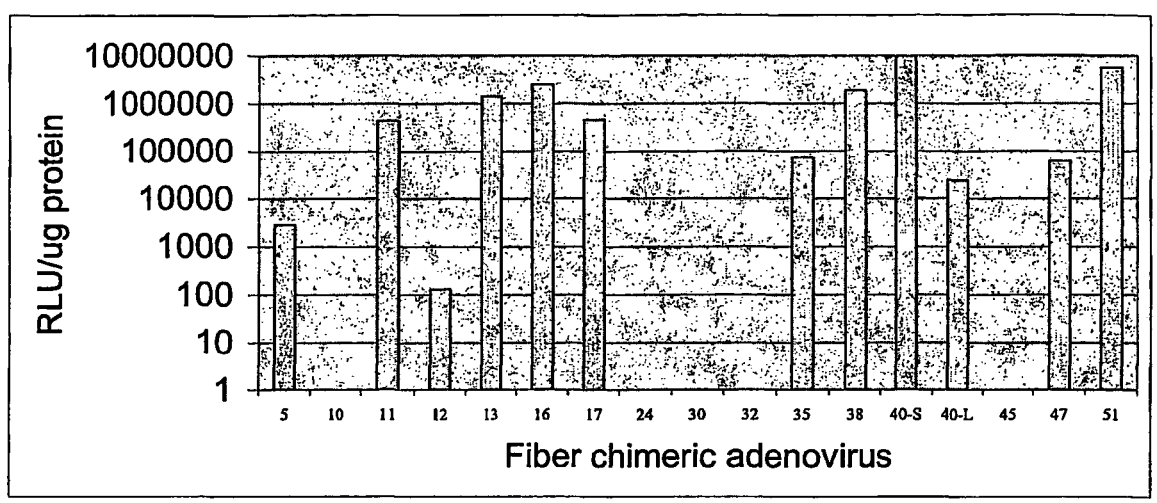

FIG. 5: Human musculus pectoralis major samples were incubated for two hours with different fiber chimaeric vectors at $10^{10}$ virus particles in 200 µl medium. Forty-eight hours after virus exposure the samples were analyzed for luciferase transgene expression. The luciferase activity expressed in relative light units (RLU) is corrected for the amount of protein present in the different lysates.

Figure 6:
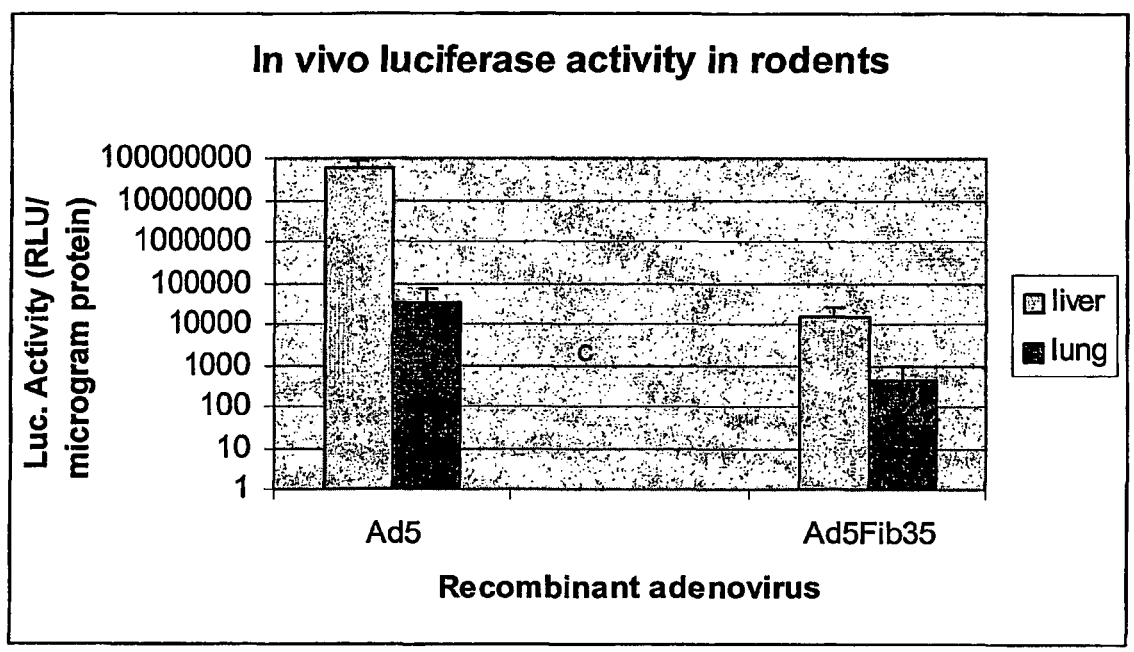

FIG. 6: In vivo luciferase activity in lung and liver cells from mice administered with Ad5 and Ad5Fib35 recombinant adenoviruses. Shown is the average luciferase activity +/− SD of ten mice per group. Values are corrected for negative control background (n=3 mice).

DETAILED DESCRIPTION

The present invention includes reference to deposited biological material. All biological material referenced herein has been deposited with the European Collection of Cell Cultures (hereinafter referred to as the ECACC), located at CAMR, Salisbury, Wiltshire SP4 OJG UK. ECACC accession numbers P97082114, P97082115, P97082116, P97082117, P97082118, P97082119, P97082120, P97082121, and P97082122 were deposited in accordance with The Budapest Treaty of 1977 on Aug. 21, 1997. ECACC accession number 96022940 was deposited in accordance with The Budapest Treaty of 1977 on Feb. 29, 1996.

The present invention provides means and methods for the efficient transduction of a skeletal muscle cell and/or a muscle cell specific precursor thereof. In one aspect the invention discloses a gene delivery vehicle for delivering a nucleic acid of interest to a skeletal muscle cell and/or a myoblast cell, comprising a recombinant adenovirus having a tropism for skeletal muscle cells and/or myoblast cells and a nucleic acid encoding at least one amino acid sequence that is able to counteract a cardiovascular disease and/or a disease which affects skeletal muscle cells and/or myoblasts. In one embodiment, said disease that affects skeletal muscle cells and/or myoblasts is Duchenne muscular dystrophin and/or is a glycogen storage disorder. Now that efficient transduction of a muscle cell and/or myoblast by a gene delivery vehicle is disclosed, it is impossible to at least in part improve the efficacy of medical applications.

For efficient transduction of skeletal muscle cells and/or myoblasts, adenoviruses are favored because of the high levels of expression. However, although transduction of a skeletal muscle cell and/or a muscle cell specific precursor thereof is possible with adenovirus serotype 5, Ad5 efficiently infects liver cells, lung epithelia and other respiratory tissues. This is a problem, because if Ad5 is used to transduce a certain nucleic acid sequence of interest to a skeletal muscle cell and/or myoblast, said nucleic acid of interest can also be expressed by liver cells and/or cells of the respiratory tract. Expression of said nucleic acid of interest in liver cells and/or cells of the respiratory tract is not desirable, because this may cause many side-effects, like lysis of said cells or lysis of cells surrounding an infected cell, depending on the transgene. This might occur for instance when dead-proteins or other apoptosis-inducing genes are being used. Another non-desired side-effect might be the triggering of immune responses towards virus-infected cells that are not present in the tissue that is being treated. Thus, preferably, a gene delivery vehicle of the invention does not infect many liver cells and/or many respiratory cells. Besides, transduction of a skeletal muscle cell and/or a muscle cell specific precursor thereof by adenovirus serotype 5 is not very efficient. Therefore, high titers of Ad5 are needed. This has similar disadvantages, for instance toxicity to cells and for instance a strong immune response.

The present invention discloses a gene delivery vehicle with a tropism for a skeletal muscle cell and/or a myoblast cell. Said skeletal muscle cell and/or myoblast cell may be a primary skeletal muscle cell and/or a primary myoblast cell. In one embodiment, the invention discloses a gene delivery vehicle comprising a recombinant adenovirus, wherein said recombinant adenovirus is a chimaeric adenovirus.

A chimaeric adenovirus comprises a chimaeric adenovirus capsid or equivalent thereof. A chimaeric adenovirus capsid comprises at least a functional part of a capsid protein that is derived from one adenovirus serotype and at least a functional part of another capsid protein that is derived from another adenovirus serotype.

In a preferred embodiment said chimaeric capsid comprises a fiber protein comprising a tropism determining part from an adenovirus serotype belonging to group B or group F, and a penton/hexon anchoring part derived from a fiber protein of adenovirus serotype 5. Said chimaeric capsid further comprises hexon and penton proteins derived from adenovirus serotype 5.

Another aspect of the present invention discloses a gene delivery vehicle comprising a recombinant adenovirus, wherein said recombinant adenovirus comprises at least a tropism determining part of an adenoviral fiber protein comprising a tropism for skeletal muscle cells and/or myoblast cells. Said tropism may be provided by at least a tropism determining part of an adenoviral fiber protein of subgroup B and/or F. Preferably, a gene delivery vehicle of the invention comprises at least part of a fiber protein of an adenovirus of serotype 11, 16, 35, 40 and/or serotype 51 or a functional derivative and/or analogue of said serotype.

In one embodiment, a gene delivery vehicle of the invention comprising an adenoviral vector comprises a deletion in the gene encoding for fiber protein. Said deletion may be replaced., on that site or on a different site of said vector, by a nucleic acid sequence encoding an amino acid sequence capable of conferring onto said gene delivery vehicle a tropism for a skeletal muscle cell and/or a myoblast. Said nucleic acid sequence preferably comprises at least a functional part of the fiber protein from an adenovirus from subgroup B or F, comprising at least the binding moiety of the fiber protein. More preferably, a gene delivery vehicle of the invention comprises, at least part of a fiber protein of an adenovirus of serotype 11, 16, 35, 40, and/or serotype 51 or a functional part, derivative and/or analogue thereof.

A gene delivery vehicle of the invention comprising at least part of the short fiber protein 40-S can be very well used for transduction of a human skeletal muscle cell. A gene delivery vehicle of the invention comprising at least part of the long fiber protein 40-L can be used for transduction of a rodent myoblast.

To reduce a strong immune response of the host, the invention also discloses a gene delivery vehicle, preferably comprising at least a functional part of the fiber protein from an adenovirus from subgroup B and/or F, more preferably comprising at least a functional part of a fiber protein of an adenovirus of serotype 11, 16, 35, 40 and/or serotype 51 or a functional derivative and/or analogue thereof, which comprises hexon and/or penton, or a functional part, derivative and/or analogue thereof, which is not derived from an adenovirus of serotype 5. Preferably, a gene delivery vehicle of the invention comprises a capsid derived from an adenovirus of subgroup B. More preferably, said capsid is derived from an adenovirus of serotype 11, 26 and/or 35, or a functional part, derivative and/pr analogue thereof.

Capsids of serotypes 11, 26, 35 and the natural occurring 11/35 chimaeric vector are less immunogenic in a human body.

A gene delivery vehicle of the invention may at least in part reduce a strong immune response, because if Ad5 is used to transduce skeletal muscle cells and/or muscle cell specific precursors thereof, an immunocompetent host will produce antibodies against Ad5. A gene delivery vehicle of the invention can be used to transduce skeletal muscle cells and/or primary myoblasts, either after a former treatment with Ad5 or instead of a treatment with Ad5. The host may already contain antibodies against the Ad5 hexon and/or penton. But these antibodies are less, if at all, able to bind hexon and/or penton of a gene delivery vehicle of the invention, which preferably comprises hexon and/or penton from an adenovirus of serotype 11, 26 and/or 35, or a functional part, derivative and/or analogue thereof. When a gene delivery vehicle of the invention is administered, the host will start producing antibodies against the new hexon and/or penton. This will take a certain amount of time. Thus, at least in the beginning of a treatment with a gene delivery vehicle of the invention, immune response may be less than it would be if Ad5 were used. Once a host has produced antibodies against a certain gene delivery vehicle of the invention, another gene delivery vehicle of the invention, comprising another hexon and/or penton or a functional part, derivative and/or analogue thereof, can be used to at least partly reduce the immune response again.

As used herein, a gene delivery vehicle is a carrier which is able to deliver at least one nucleic acid to a host cell. If a gene delivery vehicle comprises a tropism for a certain kind of host cell, said gene delivery vehicle comprises at least a high affinity to bind to said host cell. Said gene delivery vehicle may, or may not, bind to other kind of cells as well, with either the same or a different affinity. Preferably, a gene delivery vehicle of the invention has a higher affinity to skeletal muscle cells, and/or myoblasts, and/or a lower affinity to liver cells, lung epithelia and other respiratory tissues, than an adenovirus serotype 5 wild type. Use of a gene delivery vehicle of the invention for transduction of skeletal muscle cells and/or myoblasts with high efficacy, causes less toxic side-effects than would be the case if Ad5 were used, because in the present invention less virus can be used to transduce the same amount of cells.

A functional part of a molecule is a part of a molecule that comprises the same kind of properties of said molecule in kind, not necessarily in amount. A non-limiting example of a functional part of a fiber protein is a knob protein. A functional derivative of a molecule is a molecule that has been altered such that the properties of said molecule are essentially the same in kind, not necessarily in amount. A derivative can be provided in many ways. A derivative of a protein can for instance be provided through conservative amino acid substitution. A person skilled in the art is well able to generate analogous compounds of, for instance, a fiber protein and/or hexon and/or penton. This can for instance be done through screening of a peptide library. Such an analogue has essentially the same properties of the fiber protein and/or hexon and/or penton in kind, not necessarily in amount.

A gene delivery vehicle of the invention preferably comprises a vector derived from subgroup B or subgroup F adenoviruses. More preferably, said vector is derived from serotype 11, 16, 35, 40 and/or 51. After a host cell is infected by an adenovirus, a nucleic acid of interest that is delivered does not integrate into the genome of the host cell. Therefore, it is surprising that an adenoviral vector can be used for transduction of myoblasts, because if a myoblast is infected by an adenoviral vector, a nucleic acid of interest which is delivered to said myoblast is very likely to be lost in progeny muscle cells. Therefore, for a myoblast, one would be tempted to choose a method of gene delivery whereby a nucleic acid of interest is known to become part of the genome of the host cell. However, using a gene delivery vehicle of the invention we have now found that adenovirus can also be used. The high efficacy of a gene delivery vehicle of the invention apparently enables sufficient nucleic acid to enter the cells such that upon division of a myoblast cell, at least part of the progeny also comprises said nucleic acid. Thus, the present invention discloses a method of transducing a myoblast by a gene delivery vehicle of the invention. For many applications transient expression in myoblasts of exogenous genes appears to be sufficient to trigger a process, for example angiogenesis. For several other applications sustained expression is necessary, for instance when myoblasts are encapsulated in artificial polymers to allow secretion of amino acid sequences, according to the neo-organ approach. For all applications, a gene delivery vehicle of the invention can be used, since an adenovirus can be engineered to integrate into the host cell genome (Concalves et al. 2000). A gene delivery vehicle of the invention is also suitable for delivering a nucleic acid of interest to a skeletal muscle cell, because non-genomic expression is sufficient in this case. Thus, in one embodiment the invention provides a use of a gene delivery of the invention, comprising a tropism for skeletal muscle cells and/or myoblast cells, as a vehicle for delivering a nucleic acid of interest to a skeletal muscle cell and/or a myoblast cell. Said skeletal muscle cell and/or myoblast cell may be a primary cell.

In another embodiment the present invention provides methods and means by which chimaeric adenoviruses based on adenovirus serotype 5 with modified fiber genes can be generated. For this purpose, two or three plasmids, which together contain the complete adenovirus serotype 5 genome, may be constructed. From this plasmid the DNA encoding the adenovirus serotype 5 fiber protein may be removed and replaced by linker DNA sequences that facilitate easy cloning. A plasmid in which the native adenovirus serotype 5 fiber sequence is partially removed may subsequently serve as a template for insertion of DNA encoding for fiber protein derived from different adenovirus serotypes (human or animal). The DNAs derived from different serotypes may be obtained using the polymerase chain reaction technique in combination with (degenerated) oligo-nucleotides. At the former E1 location in the genome of adenovirus serotype 5, any gene of interest can be cloned. A single transfection procedure of the two or three plasmids together may result in the formation of a recombinant chimaeric adenovirus. Although successful introduction of changes in the adenovirus serotype 5 fiber and penton-base have been reported by others, the complex structure of knob and the limited knowledge of the precise amino acids interacting with CAR render such targeting approaches laborious and difficult. To overcome the limitations described above, pre-existing adenovirus fibers may be used to maximize the chance of obtaining recombinant adenovirus which can normally assemble in the nucleus of a producer cell and which can be produced on pre-existing packaging cells.

In another aspect the invention provides a use of a gene delivery vehicle of the invention for the preparation of a medicament. Of course, a gene delivery vehicle of the invention can also be used for prophylactic purposes. Therefore, in yet another aspect, the invention provides a use of a gene delivery vehicle of the invention for the preparation of a vaccine. Said gene delivery vehicle may be used for the delivery of a nucleic acid of interest to a muscle cell and/or a myoblast. Therefore, this aspect of the invention is of course particularly useful for the treatment of diseases which affect muscle cells and/or muscle cell specific precursors thereof, for instance Duchenne muscular dystrophin, or glycogen storage disorders. Said aspect of the invention is also very, useful for the treatment of a cardiovascular disease. A gene delivery vehicle of the invention is able to deliver a nucleic acid sequence efficiently. Therefore it makes a major contribution to less efficient treatments of diseases that affect muscle cells.

Alternatively, this aspect of the invention is also useful for expression of potential therapeutic genes in the muscle of which the amino acid sequence can (also) exert its action elsewhere. Thus, yet another embodiment of the invention discloses a use of a skeletal muscle cell and/or myoblast cell comprising at least one therapeutic gene, provided by a gene delivery vehicle comprising a recombinant adenovirus having a tropism for skeletal muscle cells and/or myoblast cells, for expression of a therapeutic amino acid sequence which can exert its action inside and/or outside said skeletal muscle cell and/or myoblast cell.

In yet another aspect of the invention a nucleic acid is disclosed, which encodes at least part of a gene delivery vehicle of the invention. Of course, expression of a nucleic acid of the invention is particularly useful to generate a gene delivery vehicle of the invention. Expression may be accomplished in any way known in the art.

In yet another aspect, the invention discloses an isolated cell, said cell comprising a gene delivery vehicle of the invention. Said cell may comprise a nucleic acid as described in the previous paragraph. Thus, another embodiment of the invention discloses an isolated cell, said cell comprising a nucleic acid that encodes at least part of a gene delivery vehicle of the invention.

Typically, one does not want an adenovirus batch to be administered to a host cell that contains replication competent adenovirus, although this is not always true. In general therefore it is desired to omit a number of genes (but at least one) from the adenoviral genome on the vector encoding the recombinant virus and to supply these genes in a cell in which the vector is brought to produce recombinant, adenovirus. Such a cell is usually called a packaging cell.

A gene delivery vehicle of the invention preferably comprises deletions in the E1, E2, E3 and/or E4 region. In that case, proteins that normally are encoded in said regions are not expressed in a gene delivery vehicle of the invention. To generate a new gene delivery vehicle of the invention, said protein or proteins must be produced separately. Therefore, in one embodiment the invention discloses a cell of the invention, further comprising a nucleic acid encoding an adenovirus early protein or a functional part, derivative and/or analogue thereof. Preferably said adenovirus early protein comprises an E1, E2, E3 and/or E4 region encoded protein. A nucleic acid encoding said adenovirus early protein might be located in the genome of a cell of the invention, although other locations are possible. Said adenovirus early protein may be derived from an adenovirus of subgroup B or subgroup F. Thus in another embodiment the invention discloses a cell of the invention, comprising an adenovirus early protein of an adenovirus of subgroup B or subgroup F. Typically vector and packaging cell have to be adapted to one another in that they have all the necessary elements, but that they do not have overlapping elements which lead to replication competent virus by recombination.

Of course, a gene of interest can be inserted at for instance the site of E1 of the original adenovirus from which the vector is derived. In this manner the chimaeric adenovirus to be produced can be adapted to the requirements and needs of certain hosts in need of gene therapy for certain disorders.

A cell of the invention as described in the preceding paragraph is of course particularly well suitable for the production of a gene delivery vehicle of the invention. Therefore, in another aspect the invention provides use of a cell of the invention for production of a gene delivery vehicle of the invention. A product of a cell of the invention may enable the preparation of a pharmaceutical. Thus, another aspect of the invention is use of a cell of the invention for the preparation of a pharmaceutical. In one embodiment the invention provides a use of a cell of the invention for the preparation of a vaccine.

Another aspect of the invention discloses a skeletal muscle cell and/or myoblast, provided with an additional nucleic acid encoding at least one amino acid sequence that is able to counteract a disease that affects muscle cells and/or myoblasts. Said disease may be Duchenne muscular dystrophin and/or a glycogen storage disorder. Also, said disease may be a cardiovascular disease.

In another aspect, the invention discloses a skeletal muscle cell and/or myoblast provided with at least one potential therapeutic gene of which the amino acid sequence can exert its action inside and/or outside said skeletal muscle cell and/or myoblast cell.

A skeletal muscle cell and/or myoblast cell of the invention may be a primary skeletal muscle cell and/or a primary myoblast cell. Another embodiment of the invention discloses a pharmaceutical composition comprising a gene delivery vehicle of the invention.

EXAMPLES

The examples below illustrate the present invention. They are not limiting the invention in any way. With the teaching of the present invention, a person skilled in the art can perform alternative experiments that are still in the scope of the present invention.

Example 1

Generation of Adenovirus Serotype 5 Genomic Plasmid Clones

The complete genome of adenovirus serotype 5 has been cloned into various plasmids or cosmids to allow easy modification of parts of the adenovirus serotype 5 genome retaining the capability to produce recombinant virus. For this purpose the following plasmids were generated:

1. pBr/Ad.Bam-rITR (ECACC Deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent $E.$ $coli$ DH5α (Life Techn.) and analysis of ampiciline resistant colonies, one clone was selected that showed a digestion pattern as expected for an insert extending from the BamHI site in Ad5 to the right ITR. Sequence analysis of the cloning border at the right ITR revealed that the most 3' G residue of the ITR was missing, the remainder of the ITR was found to be correct. Said missing G residue is complemented by the other ITR during replication of the virus in packaging cells.

2. pBr/Ad.Sal-rITR (ECACC Deposit P97082119)

pBr/Ad.Bam-rITR was digested with BamHI and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBr./Ad.Sal-rITR contains adeno type 5 sequences from the SalI site at bp 16746 up to and including the rITR (missing the most 3G residue)

3. pBr/Ad.Cla-Bam (ECACC Deposit P97082117)

Wild type Adeno type 5 DNA was digested with ClaI and BamHI, and the 20.6 kb fragment was isolated from gel by electro-elution. pBr322 was digested with the same enzymes and purified from agarose gel by Geneclean. Both fragments were ligated and transformed into competent DH5α. The resulting clone pBr/Ad.Cla-Bam was analysed by restriction enzyme digestion and shown to contain an insert with adenovirus sequences from bp 919 to 21566.

4. pBr/Ad.AflII-Bam (ECACC Deposit P97082114)

Clone pBr/Ad.Cla-Bam was linearized with EcoRI (in pBr322) and partially digested with AflII. After heat inactivation of AflII for 20' at 65° C. the fragment ends were filled in with Klenow enzyme. The DNA was then ligated to a blunt double stranded oligo linker containing a PacI site (as underlined)(5'-AATTGTC<u>TTAATTAA</u>CCGCTTAA-3') (SEQ. ID. NO. 2). This linker was made by annealing the following two oligonucleotides: 5'-AATTGTCTTAAT-TAACCGC-3' (SEQ. ID. NO. 3) and 5'-AATTGCGGT-TAATTAAGAC-3' (SEQ. ID. NO. 4), followed by blunting with Klenow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), religated and transformed into competent DH5α. One clone that was found to contain the PacI site and that had retained the large adeno fragment was selected and sequenced at the 5' end to verify correct insertion of the PacI linker in the (lost) AflII site.

5. pBr/Ad.Bam-rITRpac#2 (ECACC Deposit P97082120) and pBr/Ad.Bam-rITR#8' (ECACC Deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extent of nucleotide removal was followed by separate reactions on pBr322 DNA (also digested at the ClaI site), using identical buffers and conditions. Bal31 enzyme was inactivated by incubation at 75° C. for 10 min, the DNA was precipitated and resuspended in a smaller volume of TE buffer. To ensure blunt ends, DNAs were further treated with T4 DNA polymerase in the presence of excess dNTPs. After digestion of the (control) pBr322 DNA with SalI, satisfactory degradation (~150 bp) was observed in the samples treated for 10' or 15'. The 10' or 15' treated pBr/Ad.BamrITR samples were then ligated to the above described blunted PacI linkers (See pBr/Ad.AflII-Bam). Ligations were purified by precipitation, digested with excess PacI and separated from the linkers on an LMP agarose gel. After religation, DNAs were transformed into competent DH5α and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

pWE/Ad.AflII-rITR (ECACC Deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.BaM-rITR#2 digested with BamHI and PacI. These fragments were ligated together and packaged using 1 phage packaging, extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

pBr/Ad.lITR-Sal(9.4) (ECACC Deposit P97082115)

Ad5 wild type DNA was treated with Klenow enzyme in the presence of excess dNTPs and subsequently digested with SalI. Two of the resulting fragments, designated left ITR-Sal(9.4) and Sal(16.7)-right ITR, respectively, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

pBr/Ad.lITR-Sal(16.7) (ECACC Deposit P97082118)

pBr/Ad.lITR-Sal(9.4) is digested with SalI and dephosphorylated (TSAP, Life Technologies). To extend this clone up to the third SalI site in Ad5, pBr/Ad.Cla-Bam was, linearized with BamHI and partially digested with SalI. A 7.3 kb SalI fragment containing adenovirus sequences from 9462-16746 was isolated in LMP agarose gel and ligated to the SalI-digested pBr/Ad.lITR-Sal(9.4) vector fragment.

pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated a to the ClaI-digested and blunted pWE.pac vector using the Ligation Express™ kit (Clontech). After transformation of Ultracompetent XL10-Gold cells (Stratagene), clones were identified that contained the expected insert. pWE/AflII-EcoRI containes Ad5 sequences from bp 3534-27336.

Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK is an example of an adapter plasmid designed for use according to the invention in combination with the improved packaging cell lines of the invention. This plasmid was used as the starting material to make a new vector in which nucleic acid molecules comprising specific promoter and gene sequences can be easily exchanged. First, a PCR fragment was generated from pZipΔMo+PyF101(N⁻) template DNA (described in WO096/35798) with the following primers: LTR-1: 5'-CTG TAC GTA CCA GTG CAC TGG CCT AGG CAT GGA AAA ATA CAT AAC TG-3' (SEQ. ID. NO. 5) and LTR-2: 5'-GCG GAT CCT TCG AAC CAT GGT AAG CTT GGT ACC GCT AGC GTT AAC CGG GCG ACT CAG TCA ATC G-3'(SEQ. ID. NO. 6). Pwo DNA polymerase (Boehringer Mannheim) was used according to manufacturers protocol with the following temperature cycles: once 5' at 95° C.; 3' at 55° C.; and 1' at 72° C., and 30 cycles of 1' at 95° C., 1' at 60° C., 1' at 72° C., followed by once 1' at 72° C. The PCR product was then digested with BamHI and ligated into pMLP10 (Levrero et al. 1991) vector digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Next, the coding region of the murine HSA gene was inserted. pLTR10 was digested with BstBI followed by Klenow treatment and digestion with NcoI. The HSA gene was obtained by PCR amplification on pUC18-HSA (Kay et al. 1990) using the following primers: HSA1, 5'-GCG CCA CCA TGG GCA GAG CGA TGG TGG C-3' (SEQ. ID. NO. 7) and HSA2, 5'-GTT AGA TCT AAG CTT GTC GAC ATC GAT CTA CTA ACA GTA GAG ATG TAG AA-3' (SEQ. ID. NO. 8). The amplified fragment (269 bp) was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI (sticky)-SalI (blunt) fragment and cloned into the 3.5 kb NcoI (sticky)/BstBI (blunt) fragment from pLTR10, resulting in pLTR-HSA10. Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd/L420-HSA that contains convenient recognition sites for various restriction enzymes around the promoter and gene sequences. SnaBI and AvrII can be combined with HpaI, NheI, KpnI, HindIII to exchange, promoter sequences, while the latter sites can be combined with the ClaI or BamHI sites 3' from HSA coding region to replace genes in this construct. Another adapter plasmid that was designed to allow easy exchange of nucleic acid molecules was made by replacing the promoter, gene and poly (A) sequences in pAd/L420-HSA with the CMV promoter, a multiple cloning site, an intron and a poly-A signal. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP.

Generation of Recombinant Adenoviruses

To generate E1 deleted recombinant adenoviruses with the new plasmid-based system, the following constructs are prepared: a) An adapter construct containing the expression cassette with the gene of interest linearized with a restriction enzyme that cuts at the 3' side of the overlapping adenoviral genome fragment, preferably not containing any pBr322 vector sequences, and b) A complementing adenoviral genome construct pWE/Ad.AflII-rITR digested with PacI. These two DNA molecules are further purified by phenol/chloroform extraction and EtOH precipitation. Co-transfection of these plasmids into an adenovirus packaging cell line, preferably a cell line according to the invention, generates recombinant replication deficient adenoviruses by a one-step homologous recombination between the adapter and the complementing construct. Alternatively; instead of pWE/Ad.AflII-rITR other fragments can be used, e.g., pBr/Ad-.Cla-Bam digested with EcoRI and BamHI or pBr/Ad.AflII-BamHI digested with PacI and BamHI can be combined with pBr/Ad.Sal-rITR digested with SalI. In this case, three plasmids are combined and two homologous recombination events are needed to obtain a recombinant adenovirus. It is to be understood that those skilled in the art may use other combinations of adapter and complementing plasmids without departing from the present invention. A general protocol as outlined below and meant as a non-limiting example of the present invention has been performed to produce several recombinant adenoviruses using various adapter plasmids and the Ad.AflII-rITR fragment; Adenovirus packaging cells (PER.C6™, ECACC deposit 96022940) were seeded in ~25 cm² flasks and the next day when they were at ~80% confluency, transfected with a mixture of DNA and lipofectamine agent (Life Techn.) as described by the manufacturer. Routinely, 40 µl lipofectamine, 4 µg adapter plasmid and 4 µg of the complementing adenovirus genome fragment AflII-rITR (or 2 µg of all three plasmids for the double homologous recombination) are used. Under these conditions transient transfection efficiencies of ~50% (48 hrs post transfection) are obtained as determined with control transfections using a pAd/CMV-LacZ adapter. Two days later, cells are passaged to ~80 cm² flasks and further cultured. Approximately five (for the single homologous recombination) to eleven days (for the double homologous recombination) later a cytopathogenic effect (CPE) is seen, indicating that functional adenovirus has formed. Cells and medium are harvested upon full CPE and recombinant virus is released by freeze/thawing. An extra amplification step in an 80 cm² flask is routinely performed to increase the yield since at the initial stage the titers are found to be variable despite the occurrence of full CPE. After amplification, viruses are harvested and plaque purified on PER.C6™ cells. Individual plaques are tested for viruses with active transgenes. Besides replacements in the E1 region it is possible to delete or replace (part of) the E3 region in the adenovirus because E3 functions are not necessary for the replication, packaging and infection of the (recombinant) virus. This creates the opportunity to use a larger insert or to insert more than one gene without exceeding the maximum package size (approximately 105% of wt genome length). This can be done, e.g., by deleting part of the E3 region in the pBr/Ad.Bam-rITR clone by digestion with XbaI and religation. This removes Ad5 wt sequences 28592-30470 including all known E3 coding regions. Another example is the precise replacement of the coding region of gp19K in the E3 region with a polylinker allowing insertion of new sequences. This, 1) leaves all other coding regions intact and 2) obviates the need for a heterologous promoter since the transgene is driven by the E3 promoter and poly (A) sequences, leaving more space for coding sequences. To this end, the 2.7 kb EcoRI fragment from wt Ad5 containing the 5' part of the, E3 region was cloned into the EcoRI site of pBluescript (KS⁻) (Stratagene). Next, the HindIII site in the polylinker was removed by digestion with EcoRV and HindII and subsequent religation. The resulting clone pBS.Eco-Eco/ad5DHIII was used to delete the gp19K coding region. Primers 1 (5'-GGG TAT TAG GCC AA AGG CGC A-3') (SEQ. ID. NO. 9) and 2 (5'-GAT CCC ATG GAA GCT TGG GTG GCG ACC CCA GCG-3') (SEQ. ID. NO. 10) were used to amplify a sequence from pBS.Eco-Eco/Ad5DHIII corresponding to sequences 28511 to 28734 in wt Ad5 DNA. Primers 3 (5'-GAT CCC ATG GGG ATC CTT TAC TAA GTT ACA AAG CTA-3') (SEQ. ID. NO. 11) and 4 (5'-GTC GCT GTA GTT GGA CTG G-3') (SEQ. ID. NO. 12) were used on the same DNA to amplify Ad5 sequences from 29217 to 29476. The two resulting PCR fragments were ligated together by virtue of the new introduced NcoI site and subsequently digested with XbaI and MunI. This fragment was then ligated into the pBS.Eco-Eco/ad5ΔHIII vector that was digested with XbaI (partially) and MunI generating pBS.Eco-Eco/ad5ΔHIII.Δgp19K. To allow insertion of foreign genes into the HindIII and BamHI site, an XbaI deletion was made in pBS.Eco-Eco/ad5ΔHIII.Δgp19K to remove the BamHI site in the Bluescript polylinker. The resulting plasmid pBS.Eco-Eco/ad5ΔHIIIΔgp19KΔXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is recloned into pBS.Eco-Eco/ad5ΔHIII.Δgp19K using HindIII and for example MunI. Using this procedure, we have generated plasmids expressing HSV-TK, human IL-1a, rat IL-3, luciferase or LacZ. The unique SrfI and NotI sites in the pBS.Eco-Eco/ad5ΔHIII.Δgp19K plasmid (with or without inserted gene of interest) are used to transfer the region comprising the gene of interest into the corresponding region of pBr/Ad.Bam-rITR, yielding construct pBr/Ad-.Bam-rITRΔgp19K (with or without inserted gene of interest). This construct is used as described supra to produce recombinant adenoviruses. In the viral context, expression of inserted genes is driven by the adenovirus E3 promoter. Recombinant viruses that are both E1 and E3 deleted are generated by a double homologous recombination procedure as described above for E1-replacement vectors using a plasmid-based system consisting of: a) an adapter plasmid for E1 replacement according to the invention, with or without insertion of a first gene of interest, b) the pWE/Ad.AflII-EcoRI fragment, and c) the pBr/Ad.Bam-rITRΔgp19K plasmid with or without insertion of a second gene of interest. In addition to manipulations in the E3 region, changes of (parts of) the E4 region can be accomplished easily in pBr/Ad.Bam-rITR. Generation and propagation of such a virus, however, in some cases demands complementation in trans.

Example 2

Generation of Adenovirus Serotype 5 Based Viruses with Chimaeric Fiber Proteins The method described infra to generate recombinant adenoviruses by co-transfection of two, or more seperate cloned adenovirus sequences. One of these cloned adenovirus sequences was modified such that the adenovirus serotype 5 fiber DNA was deleted and substituted for unique restriction sites thereby generating "template clones" which allow for the easy introduction of DNA sequences encoding for fiber protein derived from other adenovirus serotypes.

Generation of Adenovirus Template Clones Lacking DNA Encoding for Fiber

The fiber coding sequence of adenovirus serotype 5 is located between nucleotides 31042 and 32787. To remove the adenovirus serotype 5 DNA encoding fiber we started with construct pBr/Ad.Bam-rITR. First a NdeI site was removed from this construct. For this purpose, pBr322 plasmid DNA was digested with NdeI after which protruding ends were filled using Klenow enzym. This pBr322 plasmid was then re-ligated, digested with NdeI and transformed into *E. coli* DH5α. The obtained pBr/ΔNdeI plasmid was digested with ScaI and SalI and the resulting 3198 bp vector fragment was ligated to the 1534.9 bp ScaI-SalI fragment derived from pBr/Ad.BamrITR, resulting in plasmid pBr/Ad.Bam-rITRΔNdeI which hence contained a unique NdeI site. Next a PCR was performed with oligonucleotides NY-up: 5'-CGA CAT ATG TAG ATGCAT TAG TTT GTG TTA TGT TTC AAC GTG-3' (SEQ. ID. NO. 13) and NY-down: 5'-GGA GAC CAC TGC CAT GTT-3'(SEQ. ID. NO. 14). During amplification, both a NdeI (bold face) and a NsiI restriction site (underlined) were introduced to facilitate cloning of the amplified fiber DNAs. Amplification consisted of 25 cycles of each 45 sec. at 94° C., 1 min. at 60° C., and 45 sec. at 72° C. The PCR reaction contained 25 pmol of oligonucleotides NY-up or NY-down, 2 mM dNTP, PCR buffer with 1.5 mM MgCl$_2$, and 1 unit of Elongase heat stable polymerase (Gibco, The Netherlands). 10% of the PCR product was run on an agarose gel that demonstrated that the expected DNA fragment of ±2200 bp was amplified. This PCR fragment was subsequently purified using Geneclean kit system (Bio101 Inc.). Then, both the construct pBr/Ad.Bam-rITRΔNdeI as well as the PCR, product was digested with restriction enzymes NdeI and SbfI. The PCR fragment was subsequently cloned using T4 ligase enzyme into the NdeI and SbfI digested pBr/Ad.Bam-rITRΔNdeI, generating pBIr/Ad.BamRΔFib. This plasmid allows insertion of any PCR amplified fiber sequence through the unique NdeI and NsiI sites that are inserted in place of the removed fiber sequence. Viruses can be generated by a double homologous recombination in packaging cells described infra using an adapter plasmid, construct pBr/Ad.AflII-EcoRI digested with PacI and EcoRI and a pBr/Ad.BamRΔFib construct in which heterologous fiber sequences have been inserted. To increase the efficiency of virus generation, the construct pBr/Ad.BamRΔFib was modified to generate a PacI site flanking the right ITR. Hereto, pBr/Ad.BamRΔFib was digested with AvrII and the 5 kb adenovirus fragment was isolated and introduced into the vector pBr/Ad.Bam-rITR.pac#8 replacing the corresponding AvrII fragment. The resulting construct was named pBr/Ad.BamRΔFib.pac. Once a heterologous fiber sequence is introduced in pBr/Ad.BamRΔFib.pac, the fiber modified right hand adenovirus clone may be introduced into a large cosmid clone as described for pWE/Ad.AflII-rITR in example 1. Such a large cosmid clone allows generation of adenovirus by only one homologous recombination making the process extremely efficient.

Amplification of Fiber Sequences from Adenovirus Serotypes

To enable amplification of the DNAs encoding fiber protein derived from alternative serotypes degenerate oligonucleotides were synthesized. For this purpose, first known DNA sequences encoding for fiber protein of alternative serotypes were aligned to identify conserved regions in both the tail-region as well as the knob-region of the fiber protein. From the alignment, which contained the nucleotide sequence of 19 different serotypes representing all 6 subgroups, (degenerate) oligonucleotides were synthesized (table 2). Also depicted in table 2 is the combination of oligonucleotides used to amplify DNA encoding fiber protein of a specific serotype. The amplification reaction (50 μl) contained 2 mM dNTPs, 25 pmol, of each oligonucleotide standard 1×PCR buffer, 1.5 mM MgCl$_2$, and 1 Unit Pwo heat stable polymerase (Boehringer) per reaction. The cycler program contained 20 cycles, each consisting of 30 sec. 94° C., 60 sec. 60-64° C., and 120 sec. At 72° C. 10% of the PCR product was run on an agarose gel which demonstrated that a DNA fragment was amplified. Of each different template, two independent PCR reactions were performed after which the independent PCR fragments obtained were sequenced to determine the nucleotide sequence. From 11 different serotypes, the nucleotide sequence could be compared to sequences present in genbank. Of all other serotypes, the DNA encoding fiber protein was previously unknown and was therefore aligned with known sequences from other subgroup members to determine homology i.e. sequence divergence. Of the 51 human serotypes known to date, we have determined the DNA sequence encoding for fiber, except for serotypes 1, 6, 18, and 26.

Generation of Fiber Chimaeric Adenoviral DNA Constructs

All amplified fiber DNAs as well as the vector (pBr/Ad.BamRΔFib) were digested with NdeI and NsiI. The digested DNAs was subsequently run on an agarose gel after which the fragments were isolated from the gel and purified using the Geneclean kit (Bio101 Inc). The PCR fragments were then cloned into the NdeI: and NsiI sites of pBr/AdBamRΔFib, thus generating pBr/AdBamRFibXX (where XX stands for the serotype number of which the fiber DNA was isolated). So far the fiber sequence of serotypes 5/ 7/ 8/ 9/ 10/ 11/ 12/ 13/ 14/ 16/ 17/ 19/ 21/ 24/ 27/ 28/ 29/ 30/ 32/ 33/ 34/ 35/ 36/ 37/ 38/ 40-S/ 40-L/ 41-S/ 42/ 45/ 47/ 49/ 51 have been cloned in pBr/AdBamRFibXX. From pBr/Ad-BamRFibXX (where XX is 5/ 8/ 9/ 10/ 11/ 13/ 16/ 17/ 24/ 27/ 30/ 32/ 33/ 34/ 35/ 38/ 40-S/ 40-L/ 45/ 47/ 49/ 51) a cosmid clone in pWE/Ad.AflII-rITR (see example 1) was generated to facilitate efficient virus generation. This cosmid cloning resulted in the formation of construct pWE/Ad.AflII-rITR/FibXX (where XX stands for the serotype number of which the fiber DNA was isolated).

Generation of Recombinant Adenovirus Chimaeric for Fiber Protein

To generate recombinant Ad 5 virus carrying the fiber of serotype 12, 16, 28, 40-L, 51, and 5, three constructs, pCLIP/luciferase, pWE/AdAflII-Eco and pBr/AdBamrITR-.pac/fibXX were transfected into adenovirus producer cells. To generate recombinant Ad5 virus carrying the fiber of 5/ 7/ 8/ 9/ 10/ 11/ 12/ 13/ 14/ 16/ 17/ 19/ 21/ 24/ 27/ 28/ 29/ 30/ 32/ 33/ 34/ 35/ 36/ 37/ 38/ 40-S/ 40-L/ 41-S/ 42/ 45/ 47/ 49/

51, two contructs pCLIP/luciferase and pWE/Ad.AflII-rITR/FibXX were transfected into adenovirus producer cells. For transfection, 2 µg of pCLIP/luciferase, and 4 µg of both pWE/AdAflII-Eco and pBr/AdBamrITR.pac/fibXX (or in case of cosmids: 4 µg of pCLIP/luciferase plus 4 µg of pWE/Ad.AflII-rITR/FibXX) were diluted in serum free DMEM to 100 µl total volume. To this DNA suspension 100 µl 1× diluted lipofectamine (Gibco) was added. After 30 minutes at room temperature the DNA-lipofectamine complex solution was added to 2.5 ml of serum-free DMEM that was subsequently added to a T25 cm$^2$ tissue culture flask. This flask contained 2×10$^6$ PER.C6™ cells that were seeded 24-hours prior to transfection. Two hours later, the DNA-lipofectamine complex containing medium was diluted once by the addition of 2.5 ml DMEM supplemented with 20% fetal calf serum. Again 24 hours later the medium was replaced by fresh DMEM supplemented with 10% fetal calf serum. Cells were cultured for 6-8 days, harvested, and freeze/thawed 3 times. Cellular debris was removed by centrifugation for 5 minutes at 3000 rpm at room temperature. Of the supernatant 3-5 ml was used to again infect PER.C6 cells (T80 cm$^2$ tissue culture flasks). This re-infection resulted in full cytopathogenic effect (CPE), after 5-6 days after which the adenovirus is harvested as described above.

Example 3

Production, Purification, and Titration of Fiber Chimaeric Adenoviruses

Of the supernatant obtained from transfected PER.C6™ cells 10 ml was used to inoculate nine T175 flasks containing 1.5×10$^6$ cells/ml PER.C6™. Three days after inoculation, the cells were trypsinised and pelleted by centrifugating for 10 min at 1750 rpm at room temperature. The chimaeric adenovirus present in the pelleted cells was subsequently extracted and purified using the following downstream processing protocol. The pellet was dissolved in 50 ml 10 mM NaPO$_4^-$ and frozen at −20° C. After thawing at 37° C., 5.6 ml deoxycholate (5% w/v) was added and the solution was homogenized. This solution was subsequently incubated for 15 min at 37° C. to completely crack the cells. After homogenizing the solution, 1875 µl (1M) MgCl$_2^-$ was added and 5 ml 100% glycerol. After the addition of 375 µl DNAse (10 mg/ml) the solution was incubated for 30 min at 37° C. Cell membranes were removed by centrifugation at 1880×g for 30 min at room temperature without the brake on. The supernatant was subsequently purified from proteins by loading on 10 ml of freon. Upon centrifugation for 15 min at 2000 rpm without brake at room temperature three bands are usually visible of which the upper band represents the adenovirus. This band was picked after which it was loaded on a Tris/HCl (1M) buffered CsCl block gradient (range: 1.2 to 1.4 gr./ml). Upon centrifugation at 21000 rpm for 2.5 hat 10° C. the virus was purified since it does not migrate into the 1.4 g/ml CsCl solution. The virus band was isolated after which a second purification using a Tris/HCl (1 M) buffered continues gradient of 1.33 g/ml of CsCl was performed. The virus was centrifuged for 17 h at 55000 rpm at 10° C. Subsequently the virus band was isolated and after the addition of 30 µl of sucrose (50 w/v) excess CsCl was removed by three rounds of dialysis, each round comprising of 1 h. For dialysis the virus was transferred to dialysis slides (Slide-a-lizer, cut off 10000 kDa, Pierce, USA). The buffers used for dialysis are PBS which are supplemented with an increasing concentration of sucrose (round 1 to 3: 30 ml, 60 ml, and 150 ml sucrose (50% w/v)/1.5 liter PBS, all supplemented with 7.5 ml 2% (w/v) CaMgCl$_2$). After dialysis, the virus was removed from the slide-a-lizer after which it was stored in portions of 25 and 100 µl at −85° C. To determine the number of virus particles per milliliter, 100 µl of the virus batch was run on a high-pressure liquid chromatograph (HPLC). The adenovirus binds to the column (anion exchange) after which it is eluted using a NaCl gradient (range 300-600 mM). By determining the area under the virus peak the number of virus particles can be calculated. To determine the number of infectious units (IU) per ml present in a virus batch, titrations are performed on 911 cells. For this purpose, 4×10$^4$ 911 cells are seeded per well of 96-well plates in rows B, D, and F in a total volume of 100 µl per well. Three hours after seeding the cells are attached to the plastic support after which the medium can be removed. To the cells a volume of 200 µl is added, in duplicate, containing different dilutions of virus (range 102 times diluted to 2×10$^9$). By screening for CPE the highest virus dilution which still renders CPE after 14 days is considered to contain at least one infectious unit. Using this observation, together with the calculated amount of virus volume present in these wells renders the number of infectious units per ml of a given virus batch. The production result i.e. virus particles per ml and IU per ml of those chimaeric adenoviruses that were produced, all with the luciferase cDNA as a marker, are shown in table 2.

Example 4

Adenovirus Transduction of Murine Myoblasts

Figure 2A:
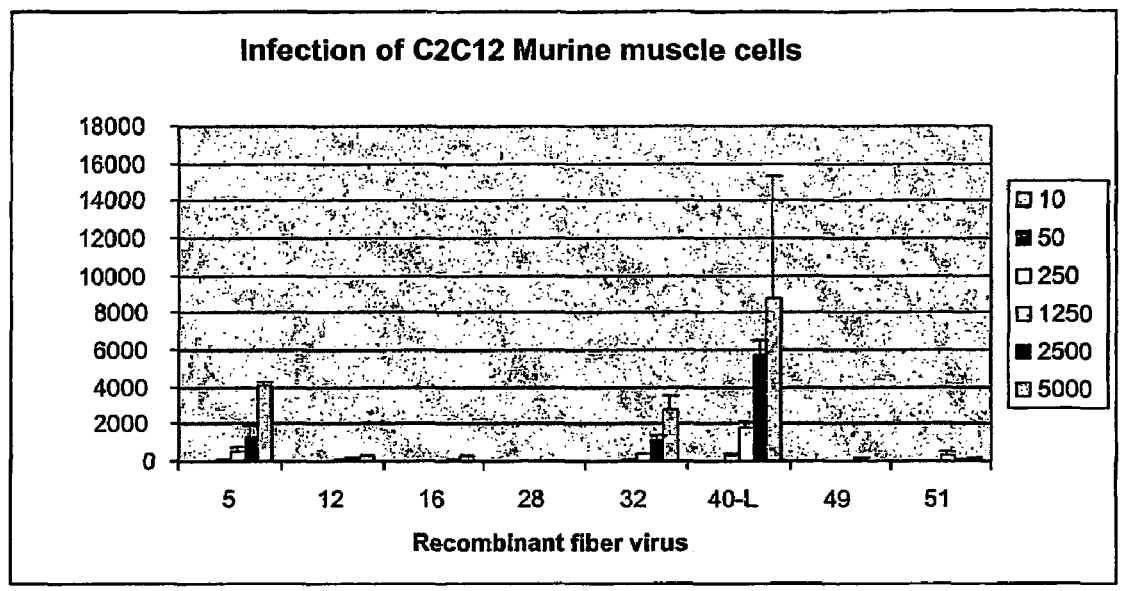
Figure 2B:
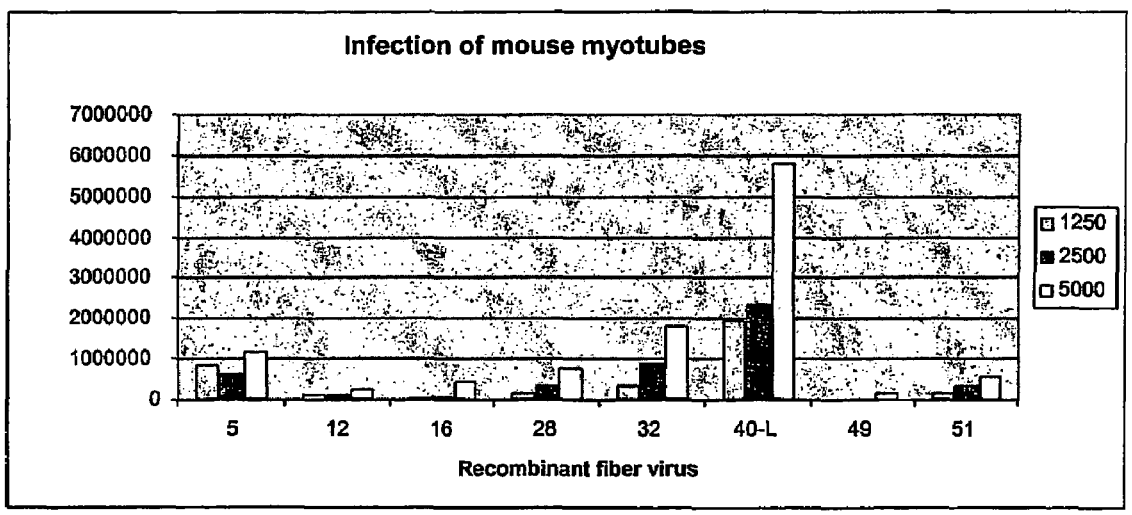

To test the viability of all fiber chimaeric vectors generated, human lung carcinoma cells (A549, ATCC) that are readily infectible with Ad5 were transduced with Ad5-based vectors carrying fiber molecules derived from alternative serotypes. Forty-eight hours after the addition of virus, cells were washed twice with 1 ml PBS after which cells were lysed by adding 100 µl of cell lysis buffer. Lysates were subsequently transferred to 96-well plates and stored at −20° C. Luciferase activity was determined using a bio-luminescence machine, the luciferase assay (Piomega™ E-1501) and the instructions provided by the manufacturer. The results shown in FIG. 1 demonstrate that a clear virus dose dependent increase in luciferase activity can be obtained on A549 cells with all vectors generated except Ad5fib12 and Ad5Fib49. Also, it becomes clear that based on the transgene expression levels measured, the efficiency of transduction differs between fiber chimaeric vectors. Next, murine C2C12 myoblasts (ATCC) which were routinely maintained in Dulbecco's modified Eagles medium (DMEM) supplemented with 10% fetal calf serum were tested. In a first experiment, 10$^5$ C2C12 cells were seeded in wells of 24-well plates. The next day cells were exposed to an increasing amount of virus particles per cell (10, 50 250, 1250, 2500, 5000) of recombinant fiber chimaeric viruses. The viruses selected for testing represent five of the six different subgroups: A (Ad5Fib12), B (Ad5Fib16 and Ad5Fib51), D (Ad5Fib28, Ad5Fib32, and Ad5Fib49) and F (Ad5Fib40-L). In this experiment, the parental Ad5 adenoviral vector was taken along as a reference and as a member of subgroup C. The results of the luciferase transgene expression measured in mouse C2C12 cells after transduction with the panel of fiber chimaeric viruses is shown in FIG. 2a. The result shows that, of the panel tested, one of the fiber chimaeric viruses (Ad5Fib40-L) perform better on C2C12 cells as compared to Ad5 yielding approximately 2-3 fold higher levels of transgene expression. In a next experiment, the same panel of fiber chimaeric viruses was tested on C2C12 cells that were cultured to high confluency such that the cells spontaneously form myotube structures. Myotubes are differentiated C2C12 cells that fuse together thus forming micro fibrils, the building blocks of skeletal muscle. This experiment on myotubes was thus performed since it better predicts the ability of the viruses to transduce mouse skeletal muscle. For this experiment C2C12 cells were again seeded at $10^5$ in wells of 247-well plates and cultured for several days until myotube structures were clearly visible. The cells of one well were counted and based on these cell counts virus particles were added to the other wells at increasing dose (1250, 2506, 5000 virus particles per cell). Forty-eight hours later cells were harvested and subjected to lysis and luciferase measurements as described above. The result of this experiment is shown in FIG. 2b. The data are in agreement with the first experiment in that Ad5Fib40-L is superior for the transduction of murine myoblasts/myotubes as compared to the Ad5 parent vector. Interestingly the level of luciferase activity measured was much higher in myotubes than on myoblasts indicative for a better transduction efficiency overall of myotubes. Clearly, these results demonstrate that the library of fiber chimaeric vectors can also be used to identify improved adenoviral vectors for the transduction of human myoblasts.

Example 5

Adenovirus Transduction of Human Myoblasts

Figure 4A:
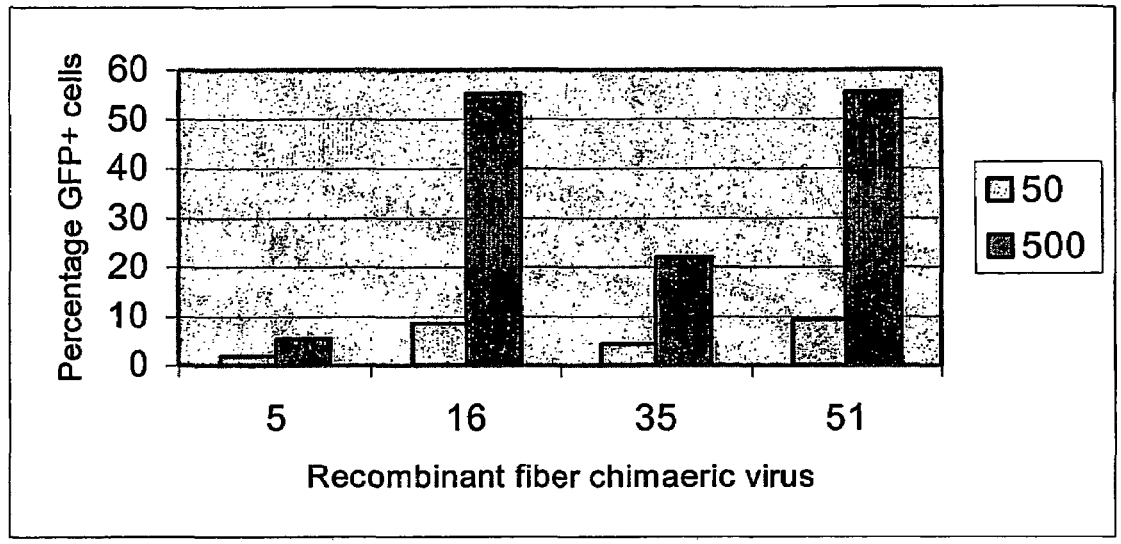
Figure 4B:
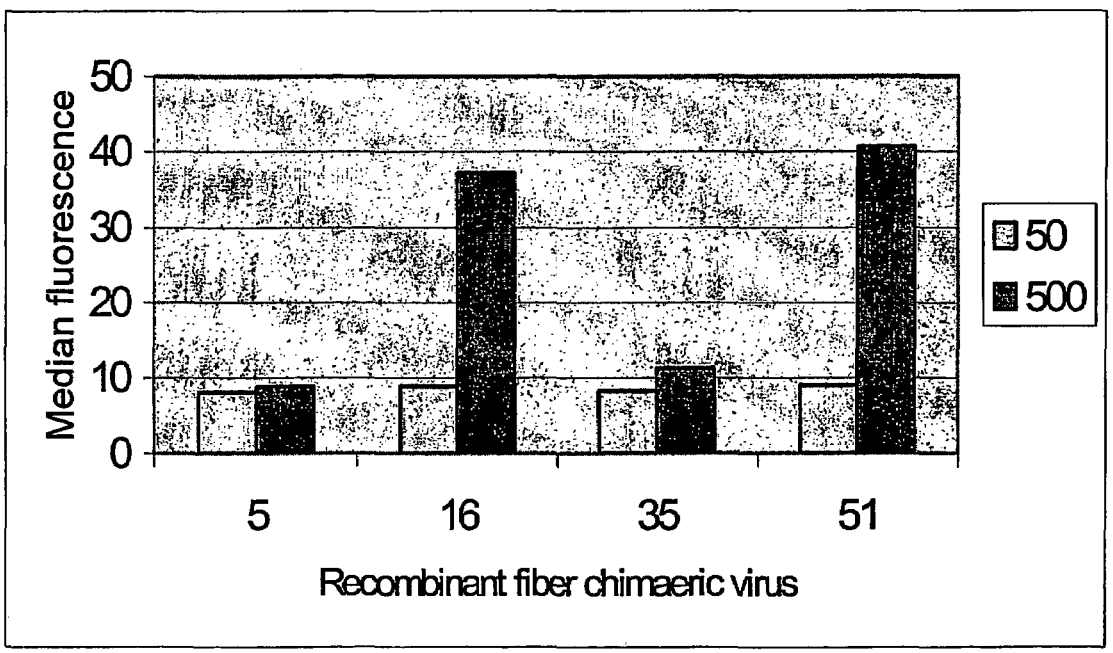

To investigate whether improved vectors for genetic modification of human myoblasts are present in the library of fiber chimaeric vectors, experiments as described under example 4 were performed on human primary myoblasts. These cells were obtained from human skeletal muscle biopsies using essentially the "explant" technique described for smooth muscle cell and endothelial cell isolation from vessels (Jaffe et al. 1973; Quax et al. 1998; Wijnberg et al. 1997). Also, human primary myoblasts were obtained commercially. (Promocell™). To test the fiber chimaeric vectors, primary myoblasts were seeded at $10^5$ cells per well of 24-well plates. Forty-eight hours after seeding, the cells were exposed to the library of fiber chimaeric vectors for 2 h. Then the virus was discarded and fresh medium was added to the cells. Forty-eight hours after virus exposure cells were harvested and luciferase activity was determined in the cell lysate as described in example 4. The results of this experiment are shown in FIG. 3. Based on the luciferase transgene expression several fiber chimaeric vectors show increased levels of transgene expression as compared to Ad5. Fiber chimaeric vectors that are superior to Ad5 for the transduction of human primary myoblasts are one subgroup D member, Ad5.Fib13 (5.7× more transgene expression and interestingly, all vectors carrying a fiber derived from subgroup B members: Ad5Fib11 (4.3×), Ad5Fib16 (6.2×), Ad5Fib35 (6.8×), and Ad5Fib51 (12.7×). In contrast to subgroup B, only Ad5Fib13 of the subgroup D fiber chimaeric vectors proved superior to Ad5. All other subgroup D fiber chimaeric vectors (Ad5.Fib10, Ad5.Fib24, Ad5.Fib27, Ad5.Fib30, Ad5.Fib33, Ad5.Fib45, Ad5.Fib47) did not perform better as compared to Ad5. In contrast to mouse C2C12 cells subgroup F derived fiber chimaeric vectors (Ad5.Fib40-L, and Ad5.Fib40-S) demonstrated only marginal higher luciferase transgene activity levels compared to Ad5. The discrepancy between the result obtained on mouse and human muscle cells can be due to the fact that receptors for these different fibers are unknown and therefore it is conceivable that receptor molecules are not conserved among species. To confirm the results obtained with the fiber chimaeric vectors carrying luciferase an identical experiment was performed as described above with a few selected fiber chimaeric adenoviruses carrying green fluorescent protein (GFP) as a marker. This marker allows single cell analysis using a flow cytometer and thus provides additional information regarding the number of cells transduced. Also, the expression level of green fluorescent protein per cell can be determined and is expressed in the median fluorescence signal intensity. Since the level of expression in a cell correlates with the number of adenoviral genomes per cell, a high level of GFP expression correlates with more successful infections as compared to a low level of GFP expression in a cell. The result of this experiment is shown in FIG. 4a (percentage of cells positive for GFP) and FIG. 4b (median fluoresce intensity signal). These results confirm earlier results in that fiber chimaeric viruses carrying the fiber from adenovirus subgroup B members (Ad5.Fib16, Ad5.Fib35, and Ad5.Fib51) are superior for the genetic modification of human myoblasts as compared to Ad5. The increase in the percentage of transgene positive cells, as compared to Ad5 was 10.2%, (Ad5Fib16), 4.1% (Ad5Fib35), and 10.3% (Ad5Fib51). Besides transducing a higher number of cells the median fluorescence, signal intensity (FIG. 4b) indicates that per cell more viruses entered leading to higher levels of GFP per cell when is using fiber chimaeric vectors carrying subgroup B fiber molecules. Because of the compact nature of skeletal muscle, transduction of myoblasts itself might not be sufficient to predict improved genetic modification after injection of an adenovirus into the skeletal muscle. Therefore, in a next experiment the library of fiber chimaeric vectors was tested on skeletal muscle tissue samples. Hereto, human skeletal muscle samples were obtained approximately 12 hours post-mortem after informed consent of the family. Part of the musculus pectoralis major was obtained of which 20 samples, each approximately 3×3×3 mm were generated. The samples were transferred to wells of 24-well plates in DMEM supplemented with 10% fetal calf serum. Each sample was exposed for two hours to one of the fiber chimaeric variants carrying luciferase ($10^{10}$ virus particles in 200 μl total medium). After two hours virus was discarded by washing after which the muscle samples were returned to the incubator in 1 ml of DMEM. After 48 h samples were minced and luciferase activity was determined in total protein lysates. The result of this experiment is shown in FIG. 5. From these experiments several observations are made. 1) In general, fiber chimaeric vectors that performed better (in terms of transgene expression) than Ad5 on cultured myoblasts also perform better on skeletal muscle biopsies. 2) On skeletal muscle tissue, Ad5Fib40-S is superior to Ad5 (3428 times increased luciferase activity) which was not observed on cultured myoblasts. 3) All fiber chimaeric vectors carrying the fiber derived from subgroup B viruses are better suited to transduce skeletal muscle as compared to Ad5. The observed increase in luciferase activity was 153× (Ad5Fib11), 868× (Ad5Fib16), 26× (Ad5.Fib35), and 1944× (Ad5.Fib51). 4) Several, but not all, chimaeric vectors carrying a fiber from subgroup D members yielded increased levels of luciferase activity. These vectors included Ad5Fib13 (495×), Ad5Fib17 (161×), Ad5Fib38 (659×), Ad5Fib47 (22×). In contrast Ad5Fib10, Ad5Fib24, Ad5Fib30, Ad5Fib32, and Ad5Fib45 (all subgroup D fibers) were not superior compared to Ad5 for the genetic modification of human skeletal muscle. The mechanism as to why these particular fibers allow Ad5 to enter skeletal muscle tissue more efficiently is unknown at present. For many of the human adenovirus serotypes the receptor(s) are currently unknown. One hypothesis for the better entry is that all the identified fiber molecules contain a relatively short shaft, thereby positioning the knob of the fiber close to the adenovirus core. The diameter of Ad5 is approximately 100 nm from which the fiber protrudes another 70 nm. In total the diameter of Ad5 is thus maximally close to 240 nm although the fiber itself is a flexible structure. With the short shaft the size of the fiber chimaeric vectors is reduced approximately 70 nm that might be sufficient to obtain an improved penetration into the skeletal muscle tissue.

Example 6

Infection of Liver and Lung Cells in Rodents Using Ad5 and Ad5Fib35 Viruses

To investigate whether a recombinant Ad5 adenoviral vector carrying a fiber derived from serotype 35 had a different infectability as compared to recombinant Ad5 with a natural capsid, the following experiment was performed. Ten BalB/C mice were administered with $10^{10}$ virus particles of recombinant Ad5 carrying a luciferase transgene and ten BalB/C mice were administered with $10^{10}$ virus particles of a luciferase carrying recombinant Ad5Fib35 batch. All mice were injected through the tail vein. 48 hours after administration the mice were sacrificed and the liver and lung cells were subsequently analyzed for luciferase activity as described in example 4. FIG. 6, shows that the Ad5Fib35 exhibits a significant lower luciferase activity in both liver and lung cells as compared to the recombinant Ad5 virus that contains an Ad5 fiber protein in its capsid. This suggests that the Ad35 fiber protein causes a decreased affinity for liver (3-log difference) and lung cells (2-log difference) when it is incorporated into the Ad5 viral particle.

REFERENCES

Akkaraju G R, Huard J, Hoffman E P, Goins W F, Pruchnic R, Watkins S C, Cohen J B and Glorioso J C (1999) Herpes Simplex virus vector-mediated dystrophin gene transfer and expression in MDX mouse skeletal muscle. J Gene Med 1:280-289

Arnberg N, Mei Y and Wadell G (1997) Fiber genes of adenoviruses with tropism for the eye and the genital tract. Virology 227:239-244

Bordet T, Smalbruch H, Pettmann B, Hagege A, Castelnau-Ptakhine L, Kahn A and Haase G (1999) Adenoviral cardiotrophin-1 gene transfer protects pnm mice from progressive motor neuronopathy. J Clin Invest 104:1077-1085

Bout A (1996) Prospects for human gene therapy. Eu J Drug Met and Pharma 2:175-179

Blaese M, Blankenstein T. Brenner M, Cohen-Hagenauer O, Gansbacher B, Russel S, Sorrentino B and Velu T (1995) Cancer Gene Ther 2:291-297

Brody S L and Crystal R G (1994) Adenovirus mediated in vivo gene transfer. Ann NY Acad Sci 716:90-101

Chao H, Samulski R, Bellinger D, Monahan P, Nicols T and Walsh C (1999) Persistent expression of canine factor IX in hemophilia B canines. Gene Ther 6:1695-1704

Chroboczek J, Ruigrok R W H and Cusack S (1995) Adenovirus fiber, p. 163-200. In: W. Doerfler and P. Bohm (ed.), The molecular repertoire of adenoviruses, I. Springer-Verlag, Berlin Dalle B, Payen E; Regulier E, Deglon N, Rouyer-Fessard P, Beuzard Y and Aebischer P (1999) Improvement of mouse beta-thalassemia upon erythropoietin delivery by encapsulated myoblasts. Gene ther 6:157-161

Defer C, Belin M, Caillet-Boudin M and Boulanger P (1990) Human adenovirus-host cell interactions; comparative study with members of subgroup B and C. J Virology 64:3661-3673

De Jong J C, Wermenbol A G, Verweij-Uijterwaai M W, Slaterus K W, Wertheim-van Dillen P, Van Doornum G J J, Khoo S H and Hierholzer, J C (1999) Adenoviruses from human immunodeficiency virus-infected individuals, including two strains that represent new candidate serotypes Ad50 and Ad51 of species B1 and D respectively, J Clin Microbiol 37:3940-3945

DiEdwardo C A, Petrosko P, Acarturk T O, DiMilla P A, LaFramboise W A and Johnson P C (1999) Muscle tissue engeneering. Clin Plast Surg 26:647-656

DiMauro S and Bruno C (1998) Glycogen storage diseases of muscle. Curr Opin Neurol 11:477-484

Francki R I B, Fauquet C M, Knudson D L and Brown. F (1991) Classification and nomenclature of viruses. Fifth report of the international Committee on taxonomy of viruses. Arch Virol Suppl 2:140-144

Goncalves M A F V, Pau M G, Valerio D and De Vries A A F (2000) Prolonged transgene expression provided by a high-capacity adeno-associated virus/adenovirus hybrid vector. Molecular Therapy Vol. 1 (no 5), abstract 351

Greber U F, Willets M, Webster P and Helenius A (1993) Stepwise dismanteling of adenovirus 2 during entry into cells. Cell 75:477-486

Hartigan-O'Connor D and Chamberlain J S (2000) Developments in gene therapy for muscular dystrophy. Microsc Res Tech 48:223-238

Hierholzer J C, Wigand R, Anderson L J, Adrian T and Gold J W M (1988) Adenoviruses from patients with AIDS: a plethora of serotypes and a description of five, new serotypes of subgenus D (types 43-47). J Infect Dis 158:804-813

Hynes R O (1992) Integrins: versatility, modulation and signalling in cell adhesion. Cell 69:11-25

Ishibashi M and Yasue H (1984) The adenoviruses, H. S. Ginsberg, ed., Plenum Press, Londen, New York. Chapter 12, 497-561

Isner J M (2000) Angiogenesis: a "breakthrough" technology in cardiovascular medicine. J Invasive Cardiol 12 supplement A, 14A-17A.

Jackson K A, Mi T and Goodell M A (1999) Hemopoietic potential of stem cells isolated from murine skeletal muscle. Proc Natl Acad Sci USA 96:14482-14486

Jaffe E A, Nachman R L, Becker C G and Minick C R (1973) Culture of endothelial cells derived from umbilical veins. Identification by morphologic and immunologic criteria. J Clin Invest 52:2745-2756

Kay R, Takei F and Humphries R K (1990) Expression cloning of a cDNA encoding M1/69. J Immunol 145: 1952-1959.

Khoo S H, Bailey A S, De Jong J C and Mandal B K (1995) Adenovirus infections in human immunodeficiency virus-positive patients: Clinical features and molecular epidemiology. J Infect Dis 172:629-637

Kidd A H, Chroboczek J, Cusack S and' Ruigrok R W (1993) Adenovirus type 40 virions contain two distinct fibers Virology 192:73-84

Krasnykh V N, Mikheeva G V, Douglas J T and Curiel D T (1996) Generation of recombinant adenovirus vectors with modified fibers for altering viral tropism. J Virol 70:6839-6846

Levrero M, Barban V, Manteca S, Ballay A, Balsamo C, Avantaggiati M L, Natoli G, Skellekens H, Tiollais P, Perricaudet M (1991) Defective and nondefective adenovirus vectors for expressing foreign genes in vitro and in vivo. Gene 101: 195-202

Li S, MacLaughlin F C, Fewell J G, Li Y, Metha V, French M F, Nordstrom J L, Coleman M, Belagali N S, Schwartz R J, Smith L C (1999) Increased level and duration of expression in muscle by co-expression of a transactivator using plasmid systems. Gene Ther 6:2005-2011, Li R H (1998) Materials for immunoisolated cell tranplantation. Adv Drug Deliv Rev 3:87-109

Li R H, Williams S, White M and Rein D (1999) Dose control with cell lines used for encapsulated cell therapy. Tissue Eng 5:453-466

MacColl G S, Goldspink G and Bouloux P M (1999) Using skeletal muscle as an artificial endocrine tissue. J Endocrinol 162:1-9

Mohajeri M H, Figlewicz D A and Bohn M C (1999) Intramuscular grafts of myoblasts genetically modified to secrete glial cell-line derived neurotropic factor prevent montneuron loss and disease progression in a mouse model of familial amyotrophic lateral sclerosis. Hum Gene Ther 20:1853-1866

Morgan C, Rozenkrantz H S and Mednis B (1969) Structure and development of viruses as observed in the electron microscope.X., Entry and uncoating of adenovirus. J Virol 4:777-796

Schratzberger P, Schratzberger G, Silver M, Curry C, Keamey M, Magner M, Alrov J, Adelman L S, Weinberg D H, Ropperr A H and Isner J M (2000) Favorable effect of VEGF gene transfer on Ischemic peripheral neuropathy. Nat Med 6:405-413

Scorsin M, Hagege A, Vilquin J T, Fiszman M, Marotte F, Samuel J L, Rappaport L, Schwartz K and Menasche P (2000) Comparison of the effect of fetal myocardiocyte and skeletal myoblast transplantation on postinfarction left ventricular function. J. Thorac Cardiovasc Surg 119: 1169-1173

Signas G, Akusjarvi G and Petterson, U (1985) Adenovirus 3 fiber polypeptide gene: Complications for the structure of the fiber protein. J Virol 53:672-678

Soreq H and Seidman S (2000) Anti-sense approach to anticholinesterase therapeutics. Isr Med Assoc J 2:81-85

Stevenson S C, Rollence M, White B., Weaver L and McClelland A (1995) Human adenovirus serotypes 3 and 5 bind to two different cellular receptors via the fiber head domain. J Virol 69:2850-2857

Stevenson S C, Rollence M, Marshall-Neff J and McClelland A (1997) Selective targeting of human cells by a chimaeric adenovirus vector containing a modified fiber protein. J Virology 71:4782-4790

Stouten P W F, Sander C, Ruigrok R W H and Cusack S (1992) New triple helical model for the shaft of the adenovirus fiber. J Mol Biol 226:1073-1084

Svensson V and Persson R (1984) Entry of adenovirus 2 into Hela cells. J Virol 51:687-694

Ueno H, Sakamoto T, Nakamura T, Qi Z, Astuchi N, Takeshita A, Shimuzu K and Ohashi H (2000) A soluble growth factor beta receptor expressed in muscle prevents liver fibrogenesis and dysfunction in rats. Hum Gene Ther 1:33-42

Varga M J, Weibull C and Everitt E (1991) Infectious entry pathway of adenovirus type 2. J Virol 65:6061-6070

Vilquin J T, Guerette B, Puymirat J, Yaffe D, Tome F M, Fardeau M, Fiszman M, Schwartz K and Tremblay J P (1999) Myoblast transplantations lead, to the expression of the laminin alpha 2 chain in normal and dystrophic (dy/dy) mouse muscles. Gene Ther 6:792-800

Wickham T J, Carrion M E and Kovesdi I (1995) Targeting of adenovirus penton base to new receptors through replacement of its RGD motif with other receptor-specific peptide motifs. Gene Therapy 2:750-756

Wijnberg M J, Quax P H A, Nieuwenbroek N M E and Verheijen J H (1997) The migration of human smooth muscle cells in vitro is mediated by plasminogen activation and can be inhibited by alpha$_2$-macroglobulin receptor associated protein. Thromb Haemostas 78:880-886

Yoo J J and Atala A (1997) A novel gene delivery system using urothelial tissue engineered neo-organs. J Urol 158:1066-1070

TABLE 1

| Syndrom | Subgenus | Serotype |
|---|---|---|
| Respiratory illness | A | 31 |
| | B | 3, 7, 11, 14, 21, 34, 35, 51 |
| | C | 1, 2, 5, 6 |
| | D | 39, 42-48 |
| | E | 4 |
| Keratoconjunctivitis (eye) | B | 11 |
| | D | 8, 19, 37, 50 |
| Hemorrhagic cystitis (Kidney) And urogenital tract infections | B | 7, 11, 14, 16, 21, 34, 35 |
| | C | 5 |
| | D | 39, 42-48 |
| Sexual transmission | C | 2 |
| | D | 19, 37 |
| Gastroenteritis | A | 31 |
| | B | 3 |
| | C | 1, 2, 5 |
| | D | 28 |
| | F | 40, 41 |
| CNS disease | A | 12, 31 |
| | B | 3, 7 |
| | C | 2, 5, 6 |
| | D | 32, 49 |
| Hepatitis | A | 31 |
| | C | 1, 2, 5 |
| Disseminated | A | 31 |
| | B | 3, 7, 11, 21 |
| | D | 30, 43-47 |
| None (???) | A | 18 |
| | D | 9, 10, 13, 15 17, 20, 22-29, 33, 36, 38 |

TABLE 2

| Adenovirus | Virus particles/ml |
|---|---|
| Ad5Fib5 | $2.2 \times 10^{12}$ |
| Ad5Fib9 | $4.9 \times 10^{11}$ |
| Ad5Fib10 | $5.5 \times 10^{11}$ |
| Ad5Fib11 | $1.1 \times 10^{12}$ |
| Ad5Fib12 | $4.4 \times 10^{12}$ |
| Ad5Fib13 | $1.1 \times 10^{12}$ |
| Ad5Fib16 | $1.4 \times 10^{12}$ |
| Ad5Fib17 | $9.3 \times 10^{11}$ |
| Ad5Fib24 | $1.0 \times 10^{12}$ |
| Ad5Fib27 | $3.0 \times 10^{11}$ |
| Ad5Fib30 | $7.1 \times 10^{11}$ |
| Ad5Fib32 | $2.0 \times 10^{12}$ |
| Ad5Fib33 | $1.5 \times 10^{12}$ |

TABLE 2-continued

| Adenovirus | Virus particles/ml |
|---|---|
| Ad5Fib35 | $2.0 \times 10^{12}$ |
| Ad5Fib38 | $5.8 \times 10^{11}$ |
| Ad5Fib40-S | $3.2 \times 10^{10}$ |
| Ad5Fib40-L | $2.0 \times 10^{12}$ |
| Ad5Fib45 | $2.8 \times 10^{12}$ |
| Ad5Fib47 | $2.6 \times 10^{12}$ |
| Ad5Fib49 | $1.2 \times 10^{12}$ |
| Ad5Fib51 | $5.1 \times 10^{12}$ |

The invention claimed is:

1. A method of delivering a nucleic acid of interest to a human skeletal muscle cell in vitro or a human myoblast cell in vitro, the method comprising:

delivering the nucleic acid of interest to said human skeletal muscle cell or said human myoblast cell by infecting said human skeletal muscle cell in vitro or said human myoblast cell in vitro with a replication-deficient recombinant serotype 5 adenovirus, said recombinant serotype 5 adenovirus having a tropism for said human skeletal muscle cell or said human myoblast cell, said recombinant serotype 5 adenovirus comprising an adenoviral genomic nucleic acid comprising the nucleic acid of interest;

wherein said recombinant serotype 5 adenovirus comprises a fiber protein comprising a knob and a shaft region from the fiber protein of an adenovirus serotype selected from the group consisting of serotypes 11, 13, 16, 17, 35, 38, 40-S, 40-L, 47 and 51.

2. The method according to claim 1, wherein said human skeletal muscle cell or said human myoblast cell is a primary cell.

3. The method according to claim 1, wherein said recombinant adenovirus has been made replication-deficient by removal of the early E1 region from said adenoviral genomic nucleic acid.

* * * * *